United States Patent [19]
Tanaka

[11] Patent Number: 6,153,995
[45] Date of Patent: Nov. 28, 2000

[54] WATER DROP DETECTION SENSOR

[75] Inventor: Shuhei Tanaka, Osaka, Japan

[73] Assignee: Nippon Sheet Glass Co., Ltd., Osaka, Japan

[21] Appl. No.: 09/285,459

[22] Filed: Apr. 2, 1999

[30] Foreign Application Priority Data

| Apr. 3, 1998 | [JP] | Japan | 10-091807 |
| Apr. 3, 1998 | [JP] | Japan | 10-091810 |
| Apr. 14, 1998 | [JP] | Japan | 10-102506 |

[51] Int. Cl.$^7$ ............................................. G05B 5/00
[52] U.S. Cl. ..................... 318/483; 318/642; 318/480; 318/DIG. 2; 15/351.17; 307/91; 307/10.1; 307/10.8
[58] Field of Search ................... 318/483, 643, 318/480, DIG. 2; 15/250.17; 307/9.1, 10.1, 10.8; 250/227.25

[56] References Cited

U.S. PATENT DOCUMENTS

| 4,871,917 | 10/1989 | O'Farrell et al. . |
| 4,960,996 | 10/1990 | Hochstein . |
| 5,998,782 | 12/1999 | Koyama et al. ............... 250/227.25 |

FOREIGN PATENT DOCUMENTS

| 0 009 414 | 4/1980 | European Pat. Off. . |
| 44 03 221 | 1/1995 | Germany . |
| 43 33 665 | 4/1995 | Germany . |
| 43 37 835 | 5/1995 | Germany . |
| 60-216245 | 10/1985 | Japan . |
| 62-163949 | 7/1987 | Japan . |
| 6-509652 | 10/1994 | Japan . |
| 8-261974 | 10/1996 | Japan . |

*Primary Examiner*—Karen Masih
*Attorney, Agent, or Firm*—Pillsbury Madison & Sutro LLP

[57] ABSTRACT

A water drop detection sensor for detecting water drops W adhering to or present upon a windshield by detecting changes in an amount of reflection light and also for detecting the ambient brightness outside of a car or other vehicle, comprising: a windshield 2; a light emitting means 5 for introducing detection light into the windshield 2; and a light receiving means 6 for detecting reflected detection light. The reflected detection light is reflected by total internal reflection within the windshield 2, and the light emitting means 5 and said light receiving means 6 are provided on the windshield 2.

12 Claims, 17 Drawing Sheets

(b)

WATER DROP DETECTION SENSOR

BACKGROUND OF THE INVENTION

1. Field of the Invention

The present invention relates to a water drop detection sensor for detecting the presence or adhesion of water drops upon a light-permeable substrate such as a window glass used in an automobile or other vehicle. In addition, the water drop detection sensor can further detect the ambient brightness in the surroundings as well as the sound of water drops. Further, the sensor can transfer a water drop detection signal and a processed signal thereof between equipment installed within the vehicle.

2. Description of Related Art

Conventionally, attempts have been made to detect water drops present upon or adhering to the front glass (windshield) of a car so as to automatically operate or initiate a wiper, and an example of a substrate having such a detection function is known, having the structure as shown in FIG. 19 attached.

In FIG. 19, a pair of prisms 201 and 202 are attached onto the surface of a transparent substrate 200—such as a glass plate or the like—into which light from a light source 203 is introduced through the prism 201 at an incident angle such that the incident light undergoes total internal reflection. By setting the incident angle so that total internal reflection will not occur if a liquid such as water is present upon or adheres to the surface of the transparent substrate 21)0, the amount of light that undergoes the total internal reflection changes depends upon the existence of the liquid at the points of total internal reflection on the glass surface. Thereby, the existence of the liquid can be detected by detecting the amount of light received by the light-receiving element 204.

In Japanese Patent Laying-Open No. Sho 60-216245 (1985), it is disclosed that the prism is set at such an angle that the light reflected from the water drops is incident upon the light receiving element only when the water drops adhere upon the glass surface, since the sensitivity for detecting the water drops is not enough with the conventional detection methods.

Further, in Japanese Patent Laying-Open No. Sho 62-163949 (1987), there is disclosed a construction in which there are provided two light sources, wherein the incident angle of the light from one of these is set to be greater than a critical angle for the total internal reflection to occur upon the detection surface thereof, while that the light from the other source is set to be less than the critical angle for the total internal reflection to occur upon detection surface thereof, thereby enabling discrimination of the presence or absence of water drops upon a glass surface.

Furthermore, in Japanese Patent Laying-Open No. Hei 8-261974 (1996), there is also disclosed a construction in which a transparent electrode of the so-called "comb" shape is positioned inside the glass plate to detect changes in electrostatic capacity, thereby actuating (controlling) the closing or opening of a window or a heater.

Moreover, in Japanese Patent Laying-Open No. Hei 6-509652 (1994)—later a PCT application—there is also disclosed a construction of a detection unit, such as a prism, which is attached upon the interior surface of the windshield through an intermediate layer which has two adhesive surfaces. This device also detects water drops on the outside surface of the windshield and controls the operation of a wiper for the windshield depending on the detected result.

With transparent substrates having conventional optical detection methods, one or more prisms are necessary for introducing the light into the glass to undergo total internal reflection, and these prisms must be closely contacted upon the glass surface therefore requiring excessive labor and time for the fitting or mounting operation. In particular, because almost all windshields for use in a car—or other wind-shielding glass plates used in other vehicles—are designed to have a curved surface, it is difficult to contact the prism upon the glass surface closely.

Moreover, for preventing unnecessary reflection at the boundary surface between the prism and the glass, the refractive indexes of the two also must be selected so as to be as close to each other as possible (i.e., refractive index matching). For this reason, a matching layer can be provided therebetween, but this increases the number of steps for manufacturing and brings about a disadvantage in the cost.

On the contrary, the method in which the water drops are detected by the variation of electric resistance or electrostatic capacity between the electrodes, such as disclosed in Japanese Patent Laying-Open No. Hei 8-261974 (1996), is inferior in durability and sensitivity to that of the above-described optical methods. In particular, for a windshield used in a car, it is important that the detected signal corresponds to the physical conditions actually seen by the driver or co-driver, and in this sense, optical method sensing is preferable.

SUMMARY OF THE INVENTION

For resolving the problems mentioned above, according to the present invention, there is provided a water drop detection sensor for detecting plural water drops adhering to or present upon a substrate and for detecting ambient brightness, comprising:

a light-permeable substrate;

light emitting means for introducing detection light into said light-permeable substrate; and light receiving means for detecting reflected detection light, said reflected detection light being reflected by total internal reflection within said light-permeable substrate, and for detecting ambient light, wherein said light emitting means and said light receiving means are provided on said light-permeable substrate.

With this sensor, the prisms are not necessary, thereby obtaining a simple construction. Further, the light enters the window glass at a certain incident angle and undergoes total internal reflection therein, and thus it can be fully utilized. Further the detection surface for any water drops adhering on the surface of the window glass comprises a reflection surface made up of a large number of reflection points, rather than dispersed reflection points. Therefore, the area for detection of the water drops is large, compared to that when detecting only those water drops adhering to or present upon the dispersed reflection points, thus improving the precision of detection. Further, since it can detect the brightness of ambient light outside of the car or vehicle as well, the field of application of the sensor can be considerably widened.

Also, according to the present invention, there is provided a water drop detection sensor for detecting plural water drops adhering to or present upon a substrate and for detecting ambient brightness, comprising:

a light-permeable substrate including an intermediate layer therein;

light emitting means for introducing detection light into said light-permeable substrate; and light receiving means for detecting reflected detection light, said reflected detection light being reflected by total internal reflection within said light-permeable substrate, and for detecting ambient light, wherein said light receiving means is provided on said light-permeable substrate, and a portion of said intermediate layer opposing to said light receiving means is formed with a reflection layer, in which layer is formed an opening for receiving the ambient light.

With this, since said light receiving means is provided on said light-permeable substrate, and a portion of said intermediate layer opposite to said light receiving means is formed with a reflection layer, in which layer is formed an opening for receiving the ambient light, the light emitted from the light emitting means is prevented from escaping outside of said light-permeable substrate without being reflected by total internal reflection therein, and also the ambient light is prevented from being excessively applied to the light receiving means, thereby enabling sufficient light to be received so as to detect the ambient brightness.

Further, according to the present invention, there is provided a water drop detection sensor for detecting plural water drops adhering to or present upon a substrate and also for detecting ambient brightness, comprising:

a light-permeable substrate;

light emitting means for introducing detection light into said light-permeable substrate;

light receiving means for detecting reflected detection light, said reflected detection light being reflected by total internal reflection within said light-permeable substrate; and, ambient light receiving means for detecting ambient light, wherein said light receiving means and said ambient light receiving means are provided on said light-permeable substrate.

With -this, since the ambient light receiving means is provided separate from the light receiving means for detecting the detection light emitted from the light emitting means, for detecting the ambient brightness, not only the ambient brightness but also any water drops adhering onto the light-permeable substrate can be detected with certainty, and the signals obtained therefrom can be processed with ease.

Further, according to the present invention, there is provided a water drop detection sensor for detecting plural water drops adhering to or present upon a substrate and also for detecting ambient brightness, comprising:

a light-permeable substrate including an intermediate layer therein;

light emitting means for introducing detection light into said light-permeable substrate;

light receiving means for detecting reflected detection light, said reflected detection light being reflected by total internal reflection within said light-permeable substrate; and ambient light receiving means for detecting ambient light, wherein said light receiving means and said ambient light receiving means are provided on said light-permeable substrate, and a portion of said intermediate layer opposing to said light receiving means is formed with a reflection layer, in which layer is formed an opening for receiving the ambient light.

With this, since a portion of said intermediate layer opposite said light receiving means is formed with a reflection layer, the light emitted from the light emitting means is prevented from escaping outside of said light-permeable substrate without also being reflected by total internal reflection therein, and also the ambient light is prevented from being applied to (incident upon) the light receiving means. In addition since the ambient light receiving means is provided separate from the light receiving means for detecting the detection light emitted from the light emitting means, for detecting the ambient brightness, not only the ambient brightness but also any water drops adhering onto the light-permeable substrate can be detected with certainty, and the signals obtained therefrom can be processed with ease.

Further, according to the present invention, there is also provided a water drop detection sensor for detecting plural water drops adhering to or present upon a substrate and also for detecting ambient brightness, comprising:

a light-permeable substrate including an intermediate layer therein, on one surface of which the water drops adhere, and on another surface of which is provided a non-pasted portion of black ceramic;

light emitting means for introducing detection light into said light-permeable substrate;

light receiving means for detecting reflected detection light, said reflected detection light being reflected by total internal reflection at plural reflection points in the non-pasted portion of black ceramic within said light-permeable substrate; and ambient light receiving means for detecting ambient light, wherein said ambient light receiving means is provided in said non-pasted portion of black ceramic through an air layer.

With this, the light emitting means, the light receiving means, and the ambient light receiving means are fixed on a portion pasted with a black ceramic portion in a belt-like manner at the periphery portion of the light-permeable substrate on the other surface thereof, which further can be attached together with other equipment provided within a common space in the car or vehicle, thereby contributing to saving space required for attaching. Also, since the ambient light receiving means is provided separate from the light receiving means for detecting the detection light emitted from the light emitting means, for detecting the ambient brightness, not only the ambient brightness but also any water drops adhering onto the light-permeable substrate can be detected with certainty, and the signals obtained therefrom can be processed with ease.

Further, according to the present invention, there is also provided a water drop detection sensor for detecting plural water drops adhering to or present upon a substrate and also for detecting ambient brightness, comprising:

a light-permeable substrate including an intermediate layer therein, on one surface of which the water drops adhere, and on another surface of which is provided a non-pasted portion of black ceramic;

light emitting means for introducing detection light into said light-permeable substrate;

light receiving means for detecting reflected detection light, said reflected detection light being reflected by total internal reflection at plural reflection points in the non-pasted portion of black ceramic within said light-permeable substrate; and ambient light receiving means for detecting ambient light, wherein said ambient light receiving means is provided in said non-pasted portion of black ceramic except the reflection point therein.

With this, since the ambient light receiving means is fixed except: each point on the other side of the light-permeable substrate, where the detection light experiences the total internal reflection, it can be fixed directly without provision of the air layer, thereby allowing the installation thereof to be easy. Also, since the ambient light receiving means is provided separate from the light receiving means for detecting the detection light emitted from the light emitting means, for detecting the ambient brightness, not only the ambient brightness but also any water drops adhering onto the light-permeable substrate can be detected with certainty, and the signals obtained therefrom can be processed with ease.

Furthermore, according to the present invention, there is provided a water drop detection sensor for detecting plural water drops adhering to or present upon a substrate and also for detecting ambient brightness, comprising:

a light-permeable substrate including an intermediate layer therein, on one surface of which the water drops adhere;

light emitting means for introducing detection light into said light-permeable substrate;

light receiving means for detecting reflected detection light, said Reflected detection light being reflected by total internal reflection within said light-permeable substrate; and ambient light receiving means for detecting ambient light, wherein said light emitting means, said light receiving means, and said ambient light receiving means are provided on the other side of said light-permeable substrate, and a portion of said intermediate layer is formed with a reflection layer located between said light emitting means and said light receiving means.

With this, since the light propagates within the light-permeable substrate, being reflected by total internal reflection between the boundary surface defined between the one side surface of light-permeable substrate and the air and the reflection layer alternatively, the optical path of the detection light from the light emitting means up to the light receiving means becomes shorter compared to the case where it propagates while being reflected by total internal reflection between the boundary surface defined between the one side surface of the light-permeable substrate and the air and the boundary surface defined between the other side surface thereof alternatively, thereby decreasing attenuation (loss) of the detection light.

Further, according to the present invention, there is provided a water drop detection sensor as defined above, wherein said light-permeable substrate is a windshield, and said water drop detection sensor detects an amount of water drops adhering onto said windshield to provide a control signal to a wiper driver portion, and further detects the amount of ambient light to provide a control signal to a headlight driver portion.

With this, a control signal can be provided to the wiper driver portion, depending upon the amount of water drops adhering onto the windshield, and a control signal depending upon the amount of ambient light can be provided to the headlight driver portion.

Further, according to the present invention, there is provided a water drop detection sensor as defined above, wherein said light-permeable substrate is a windshield, and said water drop detection sensor detects an amount of water drops adhering onto said windshield and an amount of ambient light to provide a control signal to a wiper driver portion.

With this, the control signals can be provided to the wiper driver portion, depending upon the amount of water drops adhering onto the windshield and upon the amount of ambient light.

Furthermore, according to the present invention, there is also provided a water drop detection sensor for detecting plural water drops adhering to or present upon a substrate and also for transferring a water drop detection signal and other signals between other equipment using radio waves, comprising:

a light-permeable substrate;

light emitting means for introducing detection light into said light-permeable substrate;

light receiving means for detecting reflected detection light, said reflected detection light being reflected by total internal reflection within said light-permeable substrate;

a transmission antenna for transmitting the signals between the other equipment using radio wave; and a signal processing portion for processing at least the water drop detection signal, wherein said light emitting means and said light receiving means are provided on said light-permeable substrate, and said transmission antenna and said signal processing portion are provided near said light emitting means and said light receiving means.

With this, the transmission antenna and the signal processing portion are provided for transmitting the water drop detection signal and the other signals between the other equipment using radio waves, and no wiring nor connector is necessitated, thereby widening the applicability of the water drop detection sensor.

Moreover, according to the present invention, there is provide a water drop detection sensor for detecting plural water drops adhering to or present upon a substrate and also for transferring a water drop detection signal and other signals between other equipment using light, comprising:

a light-permeable substrate;

light emitting means for introducing detection light into said light-permeable substrate;

light receiving means for detecting reflected detection light, said reflected detection light being reflected by total internal reflection within said light-permeable substrate; and a light transmission means for transmitting the signals between the other equipment using light waves, wherein said light emitting means and said light receiving means are provided on said light-permeable substrate, and said light transmission means is provided near said light emitting means and said light receiving means.

Also with this, the light transmission means is provided for enabling the transmission of the water drop detection signal and the others between the other equipment using light, and no wiring nor connector is necessitated, thereby widening the applicability of the water drop detection sensor.

Additionally, according to the present invention, there is further provided a water drop detection sensor for detecting plural water drops adhering to or present upon a substrate and also for transferring a water drop detection signal and other signals between other equipment using sonic waves, comprising:

a light-permeable substrate;

light emitting means for introducing detection light into said light-permeable substrate;

light receiving means for detecting reflected detection light, said reflected detection light being reflected by total internal reflection within said light-permeable substrate; and a sonic wave transmission means for transmitting the signals between the other equipment using sonic waves, wherein said light emitting means and said light receiving means are provided on said light-permeable substrate, and said sonic wave transmission means is provided near said light emitting means and said light receiving means.

Also with this, the sonic wave transmission means is provided for enabling the transmission of the water drop detection signal and the others between the other equipment using the sonic waves, and no wiring nor connector is necessitated, thereby widening the applicability of the water drop detection sensor. In addition the water drop detection sensor constructed with the light emitting means and the light receiving means, and sonic wave transmission means having the transmission function, can all be attached in a common space, thereby saving space.

Finally, according to the present invention, there is also provided a water drop detection sensor for detecting plural water drops adhering to or present upon a substrate and also for detecting the sound of water drops falling thereon, comprising:

a light-permeable substrate;

light emitting means for introducing detection light into said light-permeable substrate;

light receiving means for detecting reflected detection light, said reflected detection light being reflected by total internal reflection within said light-permeable substrate; and water drop sound detecting means for detecting the sound of water drops falling onto said light-permeable substrate, wherein said light emitting means, said light receiving means, and said water drop adhering sound detecting means are provided on said light-permeable substrate.

With this, since not only the change in the amount of reflected light due to adhesion of water drops but also the sound of the water drops falling or adhering are detected, it is possible to distinguish between changes caused by the water drops adhering onto the windshield or by dust or dirt adhering, thereby improving the certainty of the water drop detection.

DESCRIPTION OF THE PREFERRED EMBODIMENTS

Hereinafter, detailed explanation of the embodiments according to the present invention will be given by referring to the attached drawings.

Figure 1:
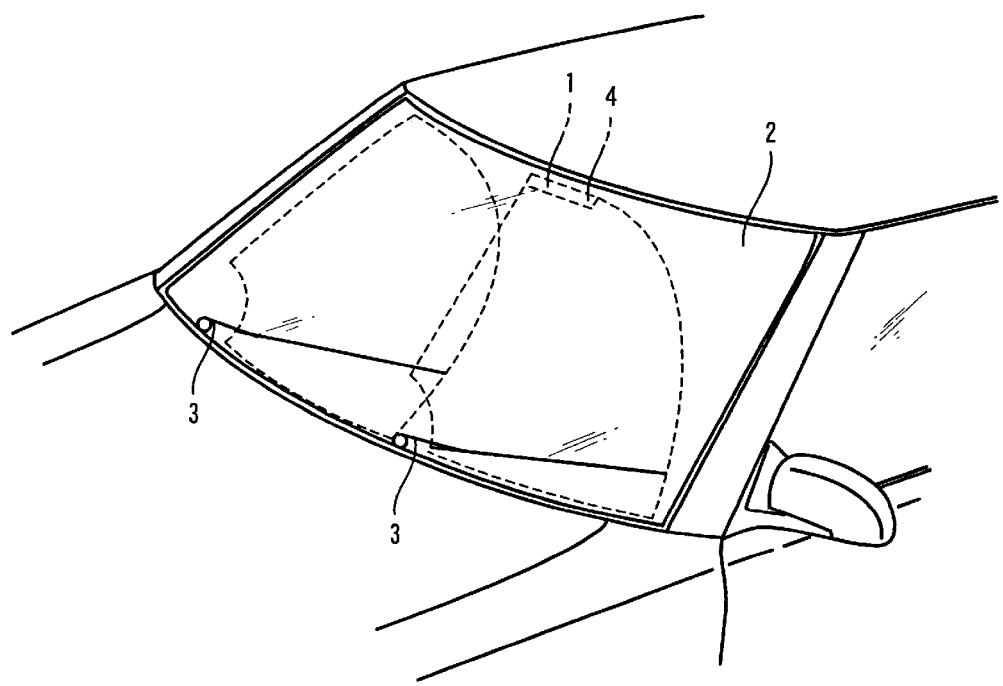
FIG. 1 is a perspective view of a front portion of a car provided with the water drop detection sensor according to the present invention.

As shown in FIG. 1, a water drop detection sensor 1 is attached or fixed on an interior surface of a windshield 2 of a car with an adhesive material 4, and the area swept by one or more external wiping blades comprises the wiping area.

The windshield 2 is made from soda lime glass having a thickness of 5 mm and mainly containing $SiO_2$, for example.

Figure 2:
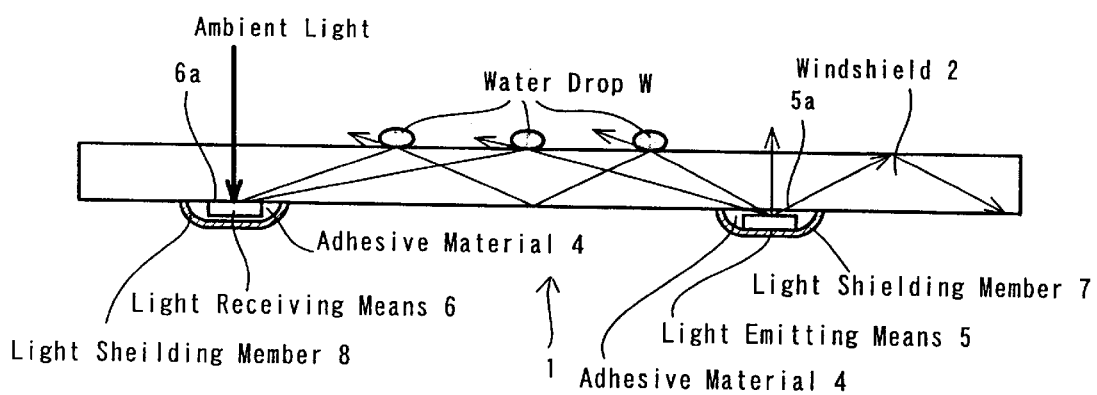
FIG. 2 is an explanatory view of the structure of the water drop detection sensor according to a first embodiment of the present invention.

As shown in FIG. 2, the water drop detection sensor 1 according to the first embodiment of the present invention comprises a light emitting means 5 for emitting detection light and a light receiving means 6 for detecting the detection light as well as for detecting ambient light outside the car. The light emitting means 5 and the light receiving means 6 are provided at a predetermined distance between them on the interior surface of the windshield 2, and both of them are bonded on the windshield 2 by a portion of adhesive material 4 so as to opposite to each other.

The reason for fixing the light emitting means 5 and the light receiving means 6 on the interior surface of the windshield 2 with the predetermined distance thereinbetween is to maintain or ensure a predetermined area (i.e., number of points where total internal reflection occurs) for detection upon the outside surface of the windshield 2, while keeping any loss of detection light emitted from the light emitting means 5 less than a predetermined level by making the light path from the light emitting means 5 to the light receiving means 6 as short as possible.

As the adhesive material 4, there is selected an adhesive such as an epoxy adhesive or an ultraviolet ray-curable epoxy adhesive, which has a refractive index approximately equal to the refractive index (1.48) of the windshield 2. Further, after adhering or affixing the light emitting means 5 and the light receiving means 6 onto the interior surface of the windshield 2 with a transparent adhesive of silicon, it is also possible to fix the light emitting means 5 and the light receiving means 6 thereto by burying them into the two portions of adhesive material 4.

Furthermore, there are provided light shielding members 7 and 8 for covering the adhesive material 4 put on the windshield 2, for fixing the light emitting means 5 and the light receiving means 6 thereto.

Both Light shielding members 7 and 8 are made of resin or metal for optically shielding the adhesive materials 4, and light shielding member 7 has the function of preventing the light emitted from the light emitting means 5 from escaping unnecessarily, while light shielding member 8 prevents external ambient light from entering into the light receiving means 6 directly from the outside.

Therefore, any light escaping from the light emitting means 5 will not propagate through the inside of the windshield 2, nor enter into the light receiving means 6 directly.

Also, each of the contacting surfaces between both light shielding members 7 and 8 and the adhesive material 4, i.e., each surface of the light shielding members 7 and 8 opposite to the light emitting means 5 and the light receiving means 6, may be light reflecting surfaces.

Further, each of the contacting surfaces between both light shielding members 7 and 8 and the adhesive material 4, i.e., each surface of the light shielding members 7 and 8 opposite to the light emitting means 5 and the light receiving means 6, may be formed with a concave mirror surface.

With the provision of the property of light reflection or the. concave mirror surface on the surface that contacts with the adhesive material 4 of the light shielding members 7 and 8 in this manner, any light emitted from the light emitting means 5 to the rear or to the sides can be collected and focused so as to propagate into the windshield 2 and be used as the detection light. Further with this, any of the emitted detection light which does not enter into the light receiving means 6 by propagating in the inside of the windshield 2 can enter into the light receiving means 6 by reflecting upon the light shielding member 8, thereby obtaining an effective utilization of the light.

Figure 3:
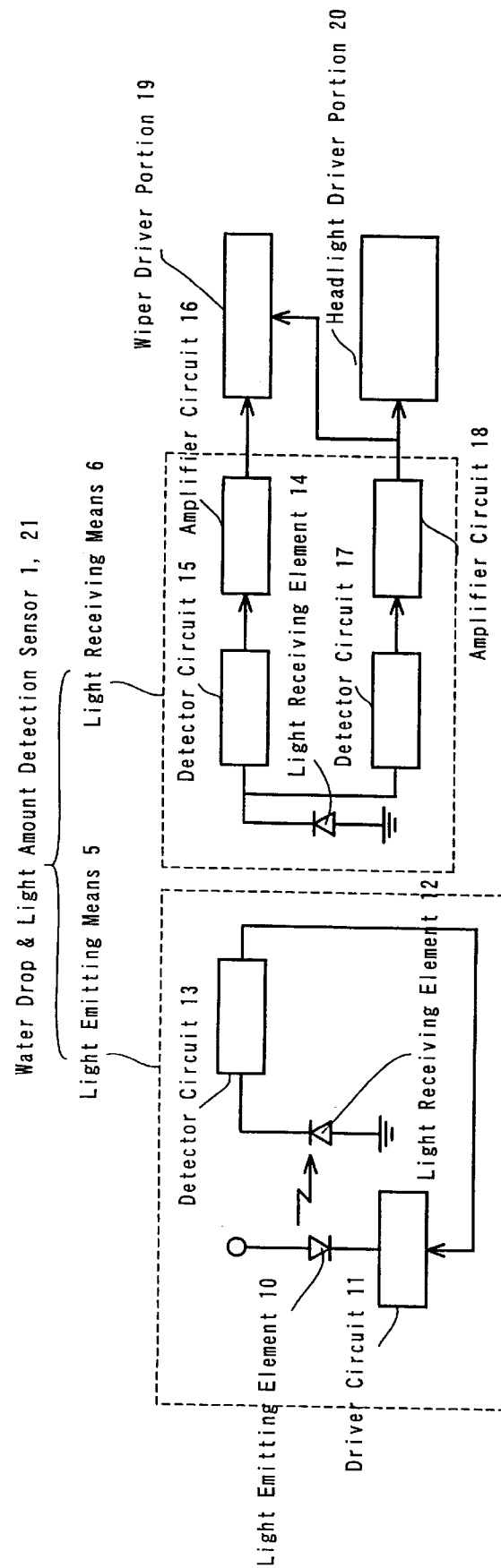
FIG. 3 is a block diagram of the water drop detection sensor according to the first or second embodiment of the present invention, applied to a wiper control system and also to a light intensity control system for a headlamp.

The light emitting means 5, as shown in FIG. 3, comprises a light emitting element 10—such as a light emitting diode (LED) or a laser diode (LE)—a driver circuit 11 for driving the light emitting element 10 to output the light which is modulated with a predetermined frequency, a light receiving element 12, such as a photo diode (PD) for monitoring the output level of the light emitting element 10, and a detector circuit 13 for removing a signal corresponding to the modulation component from the output signal of the light receiving element 12 so as to feed it back to the driver circuit 11. The driver circuit 11 controls the driving current flowing through the light emitting element 10 so as to maintain the output signal of the detector circuit 13 at a desired output level.

The Light receiving means 6, as shown in FIG. 3, comprises a light receiving element 14, such as a PD, a detector circuit 15 for removing a signal corresponding to the modulation component modulated by the driver circuit 11 of the light emitting element 10 from the output signal of the light receiving element 14, and an amplifier circuit 16 for amplifying the output signal of the detector circuit 15, and further comprises a detector circuit 17 for picking up the output signal of the light receiving element 14 due to the ambient light and an amplifier circuit 18 for amplifying and arithmetically processing an output signal of the detector circuit 17.

The output signal of the amplifier circuit 16 is inputted into a wiper driver portion 19 to be used to control the wipers 3, and the output signal of the amplifier circuit 18 is inputted into a headlight driver portion 20 to be used for the light intensity control of a headlamp provided with the car or vehicle.

Also, the output signal of the amplifier circuit 18 can be inputted into the wiper driver portion 19 to be used for the wiper control.

However, the light emitting means 5 can be constructed with only the light emitting element 10, or with the light emitting element 10 and the light receiving element 12 for monitoring, while providing the other elements—such as the driver circuit 11 and the detector circuit, etc.—in another place separately. Also, the light receiving means 6 can be constructed with only the light receiving element 14, while providing the detector circuit 16 and the amplifier circuit 18, etc., in another place separately.

Operation of the water drop detection sensor 1 constructed as described above will now be explained.

The light emitted from the light emitting means 5 is irradiated in every direction, in the case where the light emitting element 11 is an LED, or otherwise is irradiated substantially in one direction, in the case where the light emitting element 11 is an LD.

The emitted light enters the inside of the windshield 2 through the adhesive material 4, which is substantially transparent. The light emitted from the light emitting means 5, however, propagates straight on without refraction at the boundary surface between the adhesive material 4 and the windshield 2 since the adhesive material 4 is so selected to have a refraction index approximately equal to that of the windshield 2.

As shown in FIG. 2, any light entering into the inside of the windshield 2 at an incident angle less than a critical angle transmits through the windshield 2 to the outside.

Further, in a case where no water drops W adhere upon either the outside or the interior surface of the windshield 2, any light entering into the inside of the windshield 2 at an incident angle greater than the critical angle penetrates through the inside of the windshield 2 and alternately experiences total internal reflections at the boundary surface between the outside surface of the windshield 2 and the ambient air, and at the boundary surface between the interior surface of the windshield 2 and the (interior) ambient air.

That light which experiences total internal reflection inside the windshield 2 will subsequently propagate so as to enter the light receiving means 6.

Here, for obtaining the incident angle at which the total internal reflection occurs upon the boundary surface between the air and the glass, i.e., the critical angle, the following calculation can be made using Snell's law.

A general equation of Snell's law is expressed by equation 1 (Eq. 1) below, where, $\alpha$ and $\alpha_0$ represent angles with respect to a normal line on the boundary surface between two materials of refractive index n and $n_0$ ($\alpha$: incident angle, $\alpha_0$: refraction angle):

$$n_0 \sin \alpha_0 = n \sin \alpha \qquad \text{(Eq. 1)}$$

When the refractive index of the glass is n=1.48, and since the refractive index $n_0$ of air is $n_0$=1, the necessary condition for the incident angle $\alpha$ for total internal reflection to occur inside the glass is that the refraction angle $\alpha_0$ is greater than or equal to 90°, i.e. $\alpha_0 \geq 90°$. The incident angle $\alpha$ in that instance is a $\alpha \geq 42.5°$ (from Eq. 1).

Accordingly, if the incident angle $\alpha$ is equal to or greater than the critical angle (42.5°), total internal reflection occurs inside the glass medium.

On the other hand, even in a case where water (drops or other) adheres to or is present upon the glass, the condition of the incident angle $\alpha$ for total internal reflection to occur upon the boundary surface between the water and the glass inside the glass is a $\alpha \geq 64.0°$, found by making the same calculation assuming that the refractive index of water is $n_0$=1.33.

Accordingly, if the incident angle $\alpha$ is equal to or greater than the critical angle (64.0°), total internal reflection occurs inside the glass medium.

Accordingly, if the incident angle $\alpha$ lies in the region from 42.5° to 64.0° (42.5°$\leq \alpha \leq$64.0°), total internal reflection occurs inside the glass when no water adheres to or is present on the glass, while no total internal reflection occurs when the water adheres to or is present on the glass, i.e., the light escapes from the inside of the glass to the outside through the water.

For causing such a reflection, the incident angle of the light which is emitted from the light emitting means 5 is set by adjusting the position for fixing the light emitting means 5 to satisfy the condition for the incident angle $\alpha$ (42.5°$\leq \alpha \leq$64.0°). Also, since the incident angle of the reflected light entering into the light receiving means 6 is in a relationship that is symmetric with respect to the light emitting means 5, the fixing position of the light receiving means 6 is also adjusted so as to suitably receive the reflected light, avoiding any leakage thereof.

Therefore, in a case where plural water drops W adhere upon either one of the outside surface or the interior surface of the windshield 2—or upon both of them—the propagating light penetrates through the water drops W outside of the windshield 2, thereby reducing the amount of light reaching light receiving means 6.

Therefore, the quantity of plural water drops W can be detected by detecting the reduced amount of light and performing a calculation on the basis thereof.

According to the present invention, since all the light that satisfies the condition for the incident angle $\alpha$ (42.5°$\leq \alpha \leq$64.0°) can be utilized, the detection surface on which the water drops W can be detected can be a reflection surface formed from a collection of a large number of reflection points. Therefore, the area for detecting the water drops W is enlarged, compared to the case of detecting the water drops W adhering to or present upon only the reflection points, thereby improving the accuracy of detection.

As indicated in FIG. 3, the water drop detection sensor 1 provides an input to the wiper driver portion 20 with an output signal corresponding to the amount of water drops W detected.

Also, the wiper driver portion 20 initiates operation of the wiper 3 at intervals corresponding to the amount of water drops W when the detected amount of water drops W exceeds a preset value, and it stops the operation of the wiper 3 when the detected amount of water drops W comes to be less than a preset value.

Also, the light receiving means 6 detects the detection light emitted from the light emitting means 5 and also the ambient light which enters into it through the windshield 2. The ambient light is converted into a proportional electrical signal so as to detect the light amount thereof through the detector circuit 17 and the amplifier circuit 18.

The light receiving means 6 provides an output signal corresponding to the amount of ambient light to an input of the wiper driver portion 20.

The wiper driver portion 20 thus switches the headlamp into the ON condition when the ambient light detected is less than a preset value, and switches the headlamp into the OFF condition when greater than that.

As shown in FIG. 3, driving of the wiper 3 can be controlled depending upon the amount of ambient light, by providing the wiper driver portion 19 with the output signal of the amplifier 18. Very little or light rain will not obstruct a driver's vision when driving on a dark road at night. However, it does bring undesirable irregular reflection from streetlights or from the headlights of an oncoming car, contributing to the blinding of the driver.

Therefore, detecting the brightness outside the car, the wiper driver portion 19 may stop the wiper 3 only when it is decided to be non-obstructive for driving, even if the amount of water drops is equal to or greater than the preset value for operating the wiper 3 under the dark condition. On the contrary, the wiper driver portion 19 may operate the wiper 3 when the outside is bright due to streetlights or the headlights from an oncoming car, even if the amount of water drops is equal to or greater than the preset value.

Figure 4:
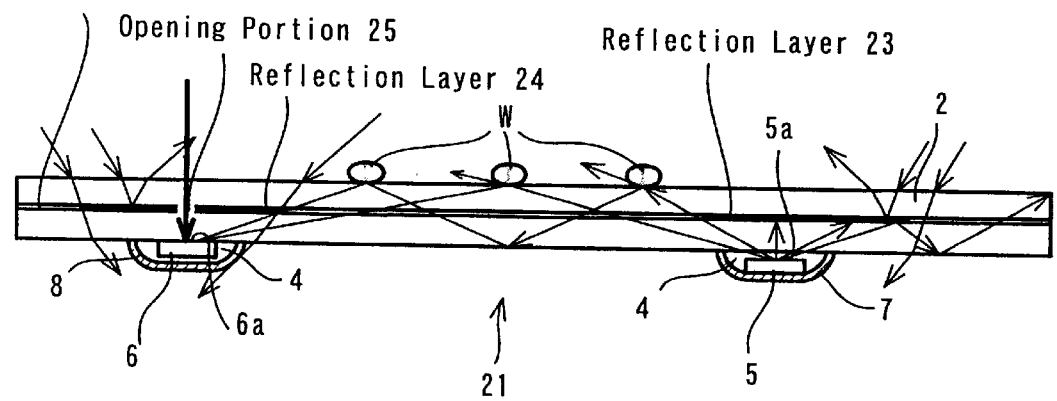
FIG. 4 is an explanatory view of the structure of the water drop detection sensor according to a second embodiment of the present invention.

As shown in FIG. 4, a water drop detection sensor 21 according to the second embodiment of the present invention comprises the light emitting means 5 and the light receiving means 6 bonded on the windshield 2 including an intermediate layer 22, wherein a reflection layer or film 23 and 24 are formed on the portions opposing a light emitting surface 5a of light emitting means 5 and opposing to a light receiving surface 6a of the light receiving means 6 on the intermediate layer 22. An opening portion 25 is formed for receiving the ambient light in the reflection layer 24 opposing the light receiving surface 6a. Shielding layers or films can be formed in place of the reflection layers 23 and 24 thereon. Further, the constructions of the other elements are the same as those of the water drop detection sensor shown in FIG. 2.

The reflection layer 23 is provided for preventing leakage of the light to the outside, which light does not experience the total internal reflection within the inside of the windshield 2 of the light emitted from the light emitting means 5.

The other reflection layer 24 is provided for preventing the light receiving means 6 from receiving any ambient light. However, it does this in such an area that it does not shield the incident light entering into the light receiving element which has experienced total internal reflection within the windshield 2.

However, since the light receiving means 6 must also receive the ambient light for detecting the brightness outside the car, the opening portion 25 formed in the reflection layer 24 is shaped so that a certain amount of ambient light can be received through it, this amount being enough only for detecting the brightness of outside light, and no more than that.

The functions of the water drop detection sensor 21 which is constructed as above are the same as those of the water drop detection sensor 1 shown in FIG. 2, except that the reflection layers 23 and 24 are formed in a part of the intermediate Layer 22, and that further the opening portion 25 is formed in the reflection layer 24 for receiving ambient light, opposing the light receiving surface 6a, thereby obtaining ambient light in an amount that is enough only for detecting the brightness of outside light, and no more than that.

Figure 5:
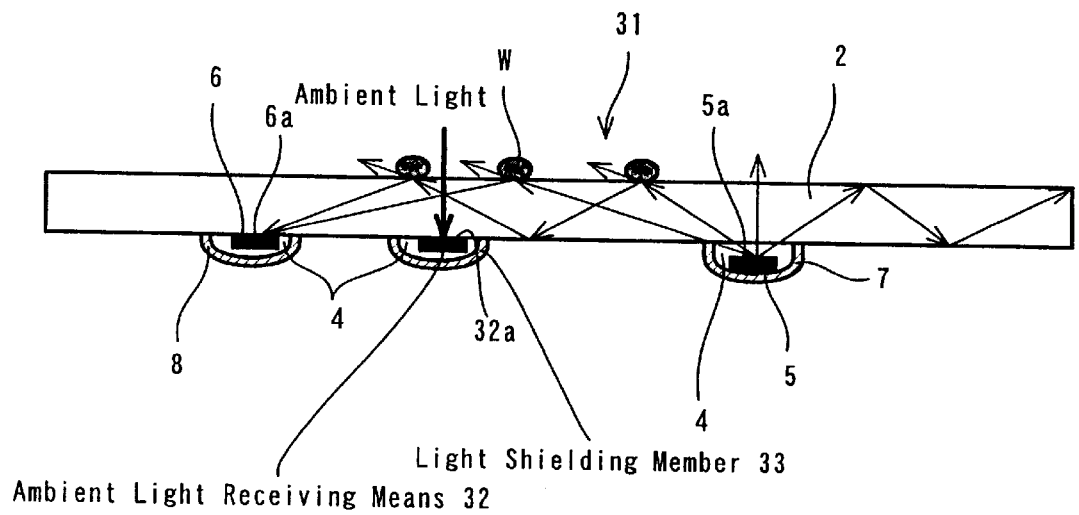
FIG. 5 is an explanatory view of the structure of the water drop detection sensor according to a third embodiment of the present invention.

As shown in FIG. 5, in the water drop detection sensor 31 according to a third embodiment of the present invention, an ambient light receiving means 32 is provided separate from the light receiving means 6, for detecting the brightness of outside ambient light, but other details of the construction are the same as that of the water drop detection sensor 1 shown in FIG. 2.

Namely, it comprises the light emitting means 5 for emitting the detection light, the light receiving means 6 for detecting that detection light, and the ambient light receiving means 32, wherein the light emitting means 5 and the light receiving 6 are separated at a predetermined distance thereinbetween at an interior side of the windshield 2 and both are fixed onto the windshield 2 with the adhesive material 4, opposing the light emitting surface 5a and the light receiving surface 6a thereof to the windshield 2.

Also, the ambient light receiving means 32 is fixed with the adhesive material 4, opposite the light receiving surface 32a thereof, in the same manner as the light receiving means 6, along a line drawn between the light emitting means 5 and the light receiving means 6 or in the vicinity thereof, and in between the light emitting means 5 and the light receiving means 6. He:re, reference numeral 33 indicates the light shielding material.

Figure 6:
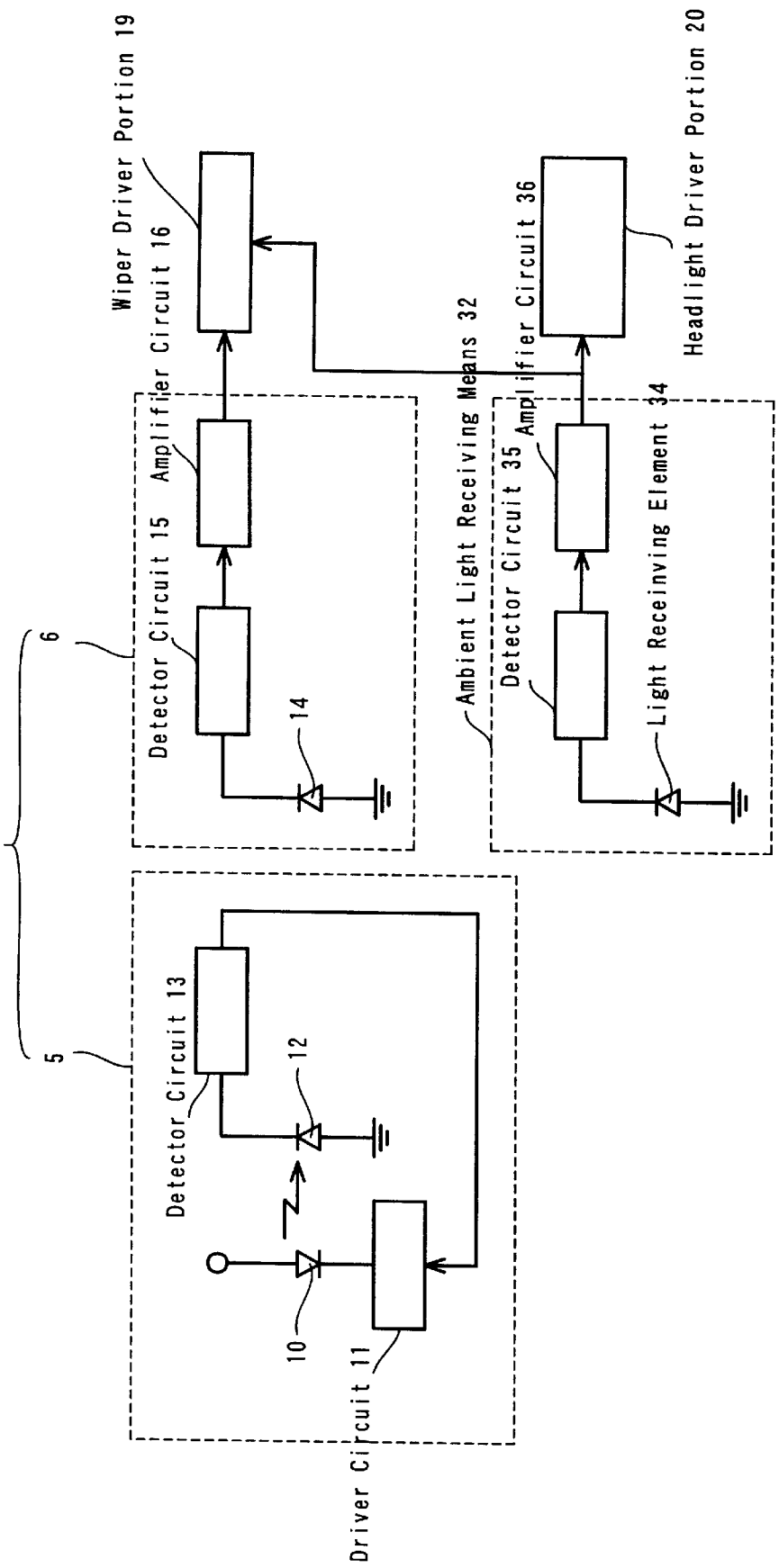
FIG. 6 is a block diagram of the structure in which the water drop detection sensor according to third through seventh embodiments of the present invention is applied to the wiper control system and the light intensity control system for a headlamp.

The light emitting means 5 is, as shown in FIG. 6, the same as the water drop detection sensor 1 and 21 shown in FIG. 3. The light receiving means 6 detects only the detection light emitted by the light emitting means 5, and comprises the light receiving element 14, such as the PD for converting the detection light into an electric signal, the detector circuit 15 for removing the signal corresponding to the modulation component due to the driver circuit 11 of the light emitting element 10 from the output signal of the light receiving element 14, and the amplifier circuit for amplifying and processing the output of the detector circuit 15.

Further, the ambient light receiving means 32 also comprises a light receiving element 34, such as the PD for converting the ambient light into an electric signal, a detector circuit 35 for removing the signal corresponding to the ambient light from the output signal of the light receiving element 34, and an amplifier circuit for amplifying and processing the output of the detector circuit 35.

The output signal of the amplifier circuit 16 is inputted to the wiper driver portion 19 to be utilized for control of the wiper, while the output signal of the amplifier circuit 35 is inputted to the headlight driver portion 20 to be utilized for control of intensity of the headlight.

The output signal of the amplifier circuit 35 may also be inputted to the wiper driver potion 19 to be utilized for control of the wiper.

However, the light emitting means 5 can be constructed with only the light emitting element 11, or with the light emitting element 11 and the light receiving element 12 for monitoring, while still providing the other elements. Also, the light receiving means 6 can be constructed with only the light receiving element 14, while providing the detector circuit 15 and the amplifier circuit 16, etc., in another place separately. The ambient light receiving means 32 also can be constructed with only the light emitting element 34, while providing the detector circuit 35 and the amplifier circuit 36, etc., in another place separately.

Explanation will be given of the operation of the water drop detection sensor 31 constructed as described above.

As shown in FIG. 6, the light receiving means 6 detects the detection light. The detection light is converted into the electric signal by the light receiving element 14, and the light amount thereof is detected by the detector circuit 15 and the amplifier circuit 16.

Then, the amplifier circuit 16 provides the wiper driver portion 19 at the input thereof with an output signal corresponding to the amount of water drops W adhering to the windshield 2.

The wiper driver portion 19 switches the wiper 3 ON with a time interval (i.e. periodic wiping or intermittent wiping) depending on the amount of water W adhering to the windshield, if the detected amount of water W adhering is equal to or greater than the preset value thereof, while it is switched OFF if the detected amount of water W is less than the preset value.

The ambient light receiving means 32 detects the ambient light introduced through the windshield 2. The ambient light is also converted into an electric signal by the light receiving element, and the light amount thereof is detected by the detector circuit 35 and the amplifier circuit 36.

Then, the amplifier circuit 36 provides the headlight driver portion 20 at the input thereof with an output signal corresponding to the amount of ambient light.

The headlight driver portion 20 turns the headlight to ON if the detected amount of ambient light is less than the preset value thereof, while it turns the headlight to OFF if the detected amount of ambient light is equal to or greater than the preset value.

Further, as shown in FIG. 6, by applying the output signal corresponding to the amount of ambient light from the amplifier circuit 36 into the input of the wiper driver circuit 19, it is possible to control the drive of the wiper 3 depending on the amount of the ambient light.

Very little or light rain will not obstruct the driver's vision on a dark road at night. However, it brings undesirable irregular reflection due to streetlights or headlights from an oncoming car, contributing to blinding the driver.

Therefore, by detecting the brightness outside the car, the wiper driver portion 19 may stop the wiper 3 only when it is determined that the level or amount of ambient light does not interfere with driving, even if the amount of any water drops present on the windshield 2 is equal to or greater than the preset value for operating the wiper 3 under the dark condition. On the contrary, the wiper driver portion 19 may operate the wiper 3 when outside ambient light is bright due to streetlights or headlights from an oncoming car, even if the amount of water drops is equal to or greater than the preset value.

However, the operation is the same as that of the water drop detection sensor 1 shown in FIG. 2, except for the function with provision of the ambient light receiving means 32 for detecting the ambient light separately other than the light receiving means 6.

Figure 7:
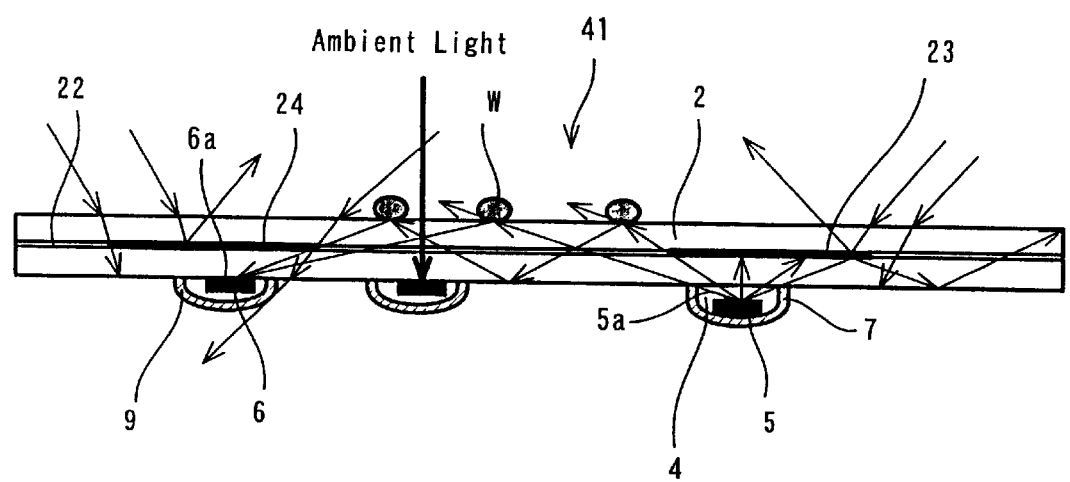
FIG. 7 is an explanatory view of the structure of the water drop detection sensor according to a fourth embodiment of the present invention.

As shown in FIG. 7, the water drop detection sensor 41 according to a fourth embodiment of the present invention is the same as the water drop detection sensor 21 shown in FIG. 4 in the construction thereof, except for the provision of the ambient light receiving means 32 for detecting the ambient light separately other than the light receiving means 6, and is also the same as the water drop detection sensor 31 shown in FIG. 5, except that the light emitting means 5, the light receiving means 6, and the ambient light receiving means 32 are fixed on the windshield 2 having the intermediate layer 22.

Explanation will be given of the operation of the water drop detection sensor 41 constructed as described above.

The ambient light receiving means 32 detects the ambient light introduced through the windshield 2. The ambient light is also converted into an electric signal by the light receiving element, and the light amount thereof is detected by the detector circuit 35 and the amplifier circuit 36.

Then, the amplifier circuit 36 provides the headlight driver portion 20 at the input thereof with an output signal corresponding to the amount of ambient light.

The headlight driver portion 20 turns the headlight ON if the detected amount of ambient light is less than the preset value thereof, while it turns the headlight OFF if the detected amount of ambient light is equal to or greater than the preset value.

However, the operation is the same as that of the water drop detection sensor 21 shown in FIG. 4 except for the function of providing the ambient light receiving means 32 for detecting the ambient light separately from the light receiving means 6.

Figure 8A:
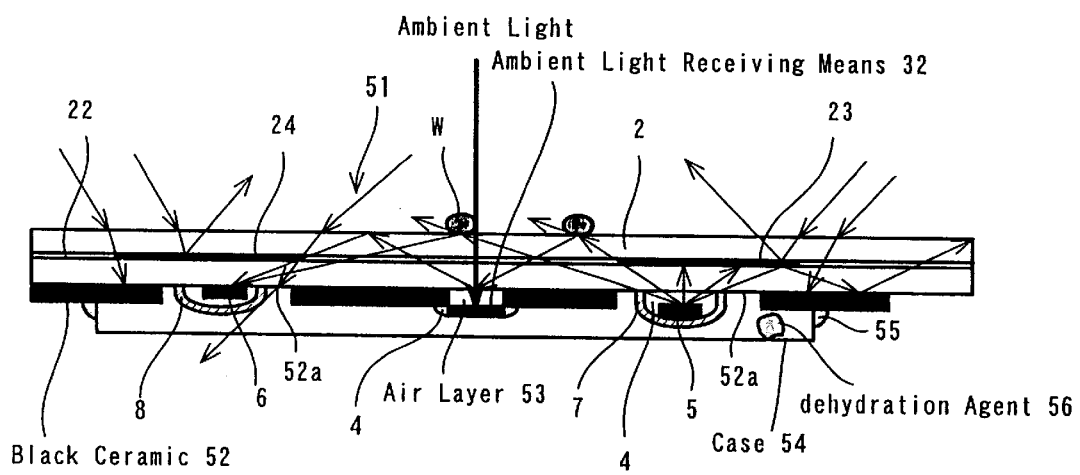
FIG. 8(a) shows a cross-section view and FIG. 8(a) a rear side view thereof.
Figure 8B:
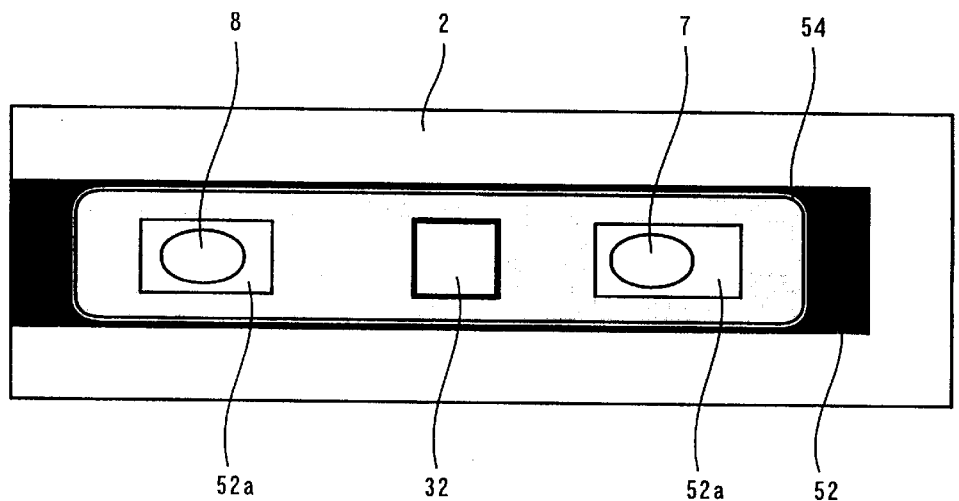
FIG. 8 is an explanatory view of the structure of the water drop detection sensor according to a fifth embodiment of the present invention, and in particular.

As shown in FIG. 8, in the water drop detection sensor 51 according to the fifth embodiment of the present invention, a belt-like black ceramic member 52 is painted or pasted onto the interior surface of the windshield 2, in particular in the periphery portion thereof, and a non-pasted portion 52a is formed in the middle of the black ceramic member 52. In the non-pasted portion 52a, the light emitting means 5 and the light receiving means 6 are fixed through the adhesive material 4.

Further, on the portion where the detection light emitted from the light emitting means 5 undergoes the total internal reflection, the non-pasted portion 52a of the black ceramic member 52 is formed for causing the total internal reflection under the same condition, forming the boundary surface between the air in the same manner as on the outside surface of the windshield 2.

In an area or portion of the non-pasted portion 52a, the ambient light receiving means 32 for detecting the brightness outside the car through an air layer 53 with the adhesive material 4 is fixed, opposite the light receiving surface on the interior side surface of the windshield 2. The air layer 53 is provided for obtaining the same condition of total infernal reflection as exists on the outer surface side of the windshield 2.

Further, the light emitting means 5, the light receiving means 6, and the ambient light receiving means 32 are covered with a case 54 of glass, resin, ceramics or metal. The case 54 is fixed on the black ceramic member 52 through a seal member 55 which also functions as adhesive material, thereby defining a sealed space enclosed by the case 54 and the windshield 2.

Within the air layer 53 defined by the interior side surface of the windshield 2 and the ambient light receiving means 32, a dehydration agent or dry air, such as a molecular sieve, is enclosed for protection from condensation of dew on the non-pasted portion 52a of the black ceramic member 52 which functions as the reflection point. Further, within the sealed space defined by the case 54 and the windshield 2, the dehydration agent 56, such as the molecular sieve or dry air, is also enclosed.

However, the construction features other than the above are the same as those of the water drop detection sensor 21 shown in FIG. 4.

The location pasted with the black ceramic member 52 of the windshield 2 where the case 53 is fixed, is also the place where an interior mirror is attached. Therefore, by utilizing a common mounting base for the interior mirror and the case, it is possible to save space for attaching both.

However, as the method for fixing or mounting the case 54 onto the black ceramic member 52, other than by fixing it with the seal member 55 having the adhering function as mentioned above, the case 54 can be fixed on a stopping member by screws at the flange portion thereof, after fixing the stopping member on the black ceramic member 52 with the adhesive material.

The function of the water drop detection sensor 51 as constructed above is the same as that of the water drop detection sensor 41 shown in FIG. 7, except for the feature of affixing the light emitting means 5 and the light receiving means 6 and the ambient light receiving means 32 in the portion of the belt-like black ceramic member 52 which is painted or pasted on the interior surface of the windshield 2.

Figure 9A:
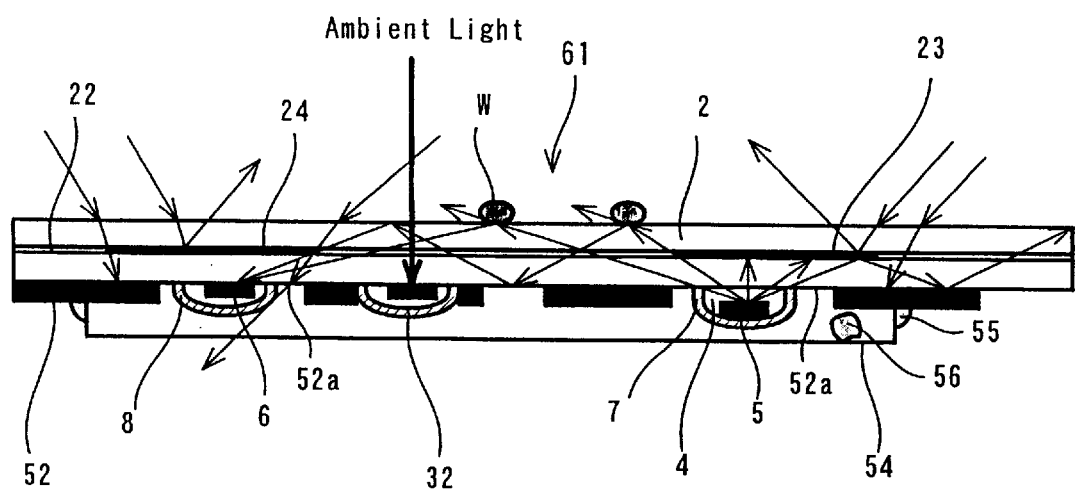
FIG. 9(a) shows the cross-section view and FIG. 9(b) the rear side view thereof.
Figure 9B:
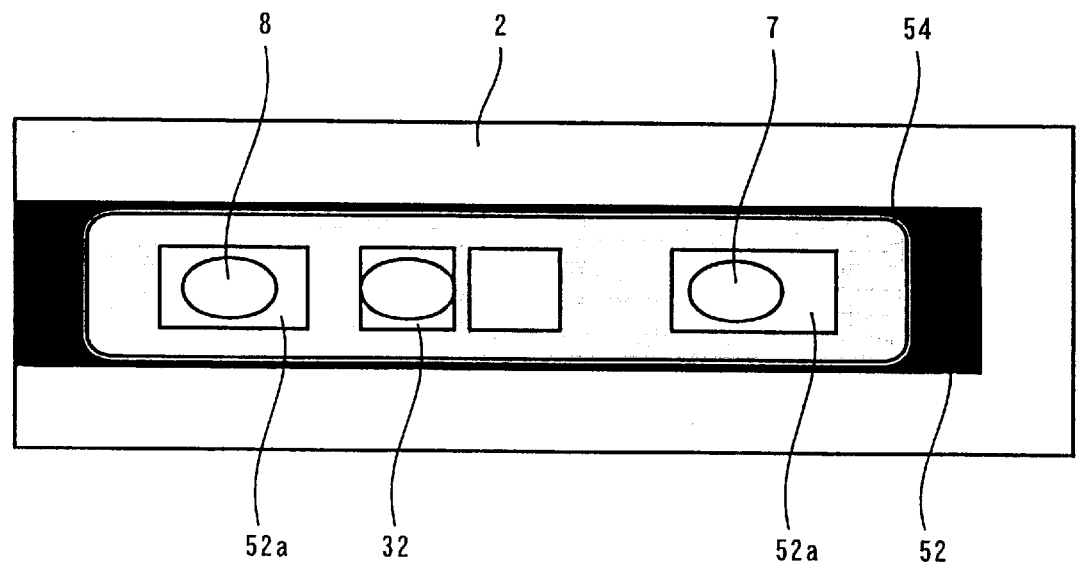
FIG. 9 is an explanatory view of the structure of the water drop detection sensor according to a sixth embodiment of the present invention, and in particular.

As shown in FIG. 9, the water drop detection sensor 51 according to a sixth embodiment of the present invention is the same as the water drop detection sensor 51 shown in FIG. 8 in the construction thereof, except for the provision of the ambient light receiving means 32 on the non-pasted portion 52a of the black ceramic member 52 with the adhesive material 4, on areas other than the portion on the interior side surface of the windshield 2 where the detection light experiences the total internal reflection.

With the provision of the ambient light receiving means 32 on areas other than the portion on the interior side surface of the windshield 2 where the detection light experiences the total internal reflection, there is no necessity to form the air layer 53 for obtaining the same total internal reflection condition as exists on the outside surface, and further the ambient light receiving means 32 can be fixed directly on the interior side surface of the windshield 2 in the same manner as the light emitting means 5 and the light receiving means 6.

The function of the water drop detection sensor 61 as constructed above is the same as that of the water drop detection sensor 51 shown in FIG. 8, except for the function due to the provision of the ambient light receiving means 32 on areas other than the portion on the interior side surface of the windshield 2 where the detection light experiences the total internal reflection.

Figure 10:
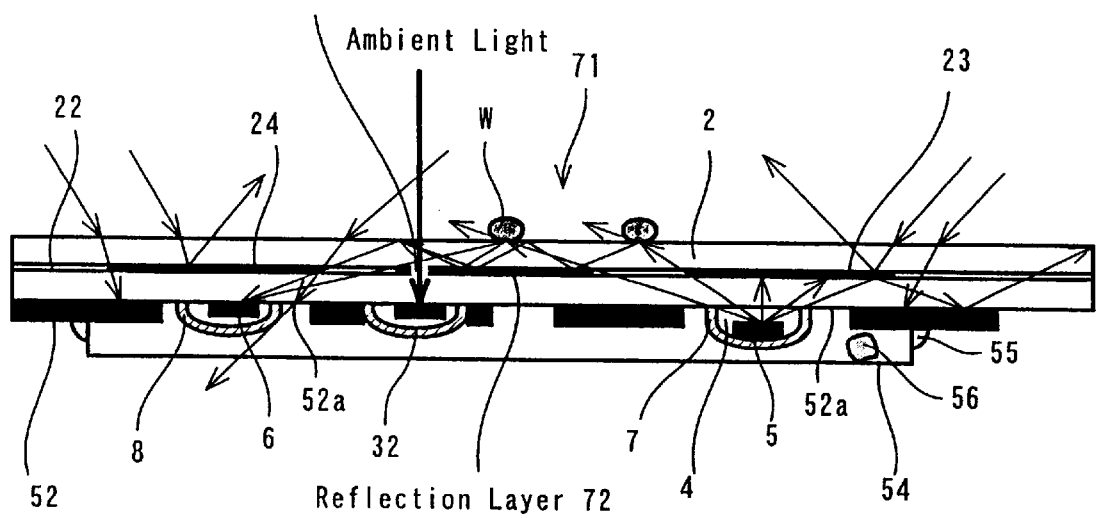
FIG. 10 is an explanatory view of the structure of the water drop detection sensor according to a seventh embodiment of the present invention.

As shown in FIG. 10, the water drop detection sensor 71 according to a seventh embodiment of the present invention is the same as the water drop detection sensor 61 shown in FIG. 9 in the construction thereof, except that the detection light from the light emitting means 5 is emitted so that it experiences total internal reflection at the boundary between the outer surface of the windshield 2 and the air, and except that the intermediate layer 22 located between the light emitting means 5 and the light receiving means 6 is formed with a reflection layer 72 in such a range that the detection light experiencing the total internal reflection will not be obstructed and can be incident upon the light receiving means 6 Further, an opening portion 73 is provided in the reflection layer 72 so that the ambient light receiving means 32 can detect the ambient light from outside the car.

Explanation will be given of the operation of the water drop detection sensor 71 constructed as described above.

By forming the intermediate layer 22 located between the light emitting means 5 and the light receiving means 6 from the reflection layer 72, light entering into the windshield 2 at an angle which is equal to or greater than the critical angle propagates inside the windshield 2, experiencing total internal reflection on the border between the outer surface of the windshield 2 and the air and on the reflection layer 72 alternatively, to be incident upon the light receiving means 6.

In this manner, by forming the intermediate layer 22 located between the light emitting means 5 and the light receiving means 6 from the reflection layer 72, the optical path for the detection light from the light emitting means 5 up to the light receiving means 6 comes to be shorter, compared to that in a case where the light experiences the total internal reflection at the border between the outer surface of the windshield 2 and the air and on the border between the interior surface thereof and the air alternatively, thereby enabling reduction in loss of the detection light. The ambient light is detected by the ambient light receiving means 32 through the opening portion 73.

However, the operation is the same as that of the water drop detection sensor 61 shown in FIG. 9, except for the feature of to forming the intermediate layer 22 located between the light emitting means 5 and the light receiving means 6 from the reflection layer 72 and forming the opening portion 73 in the reflection layer 72.

Figure 11A:
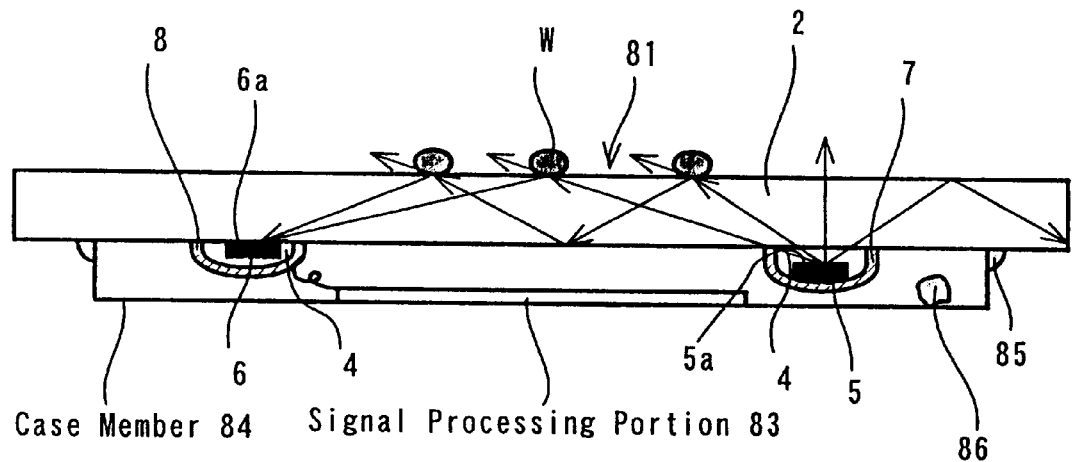
FIG. 11(a) is a cross-section view and FIG. 11(b) a rear view thereof.
Figure 11B:
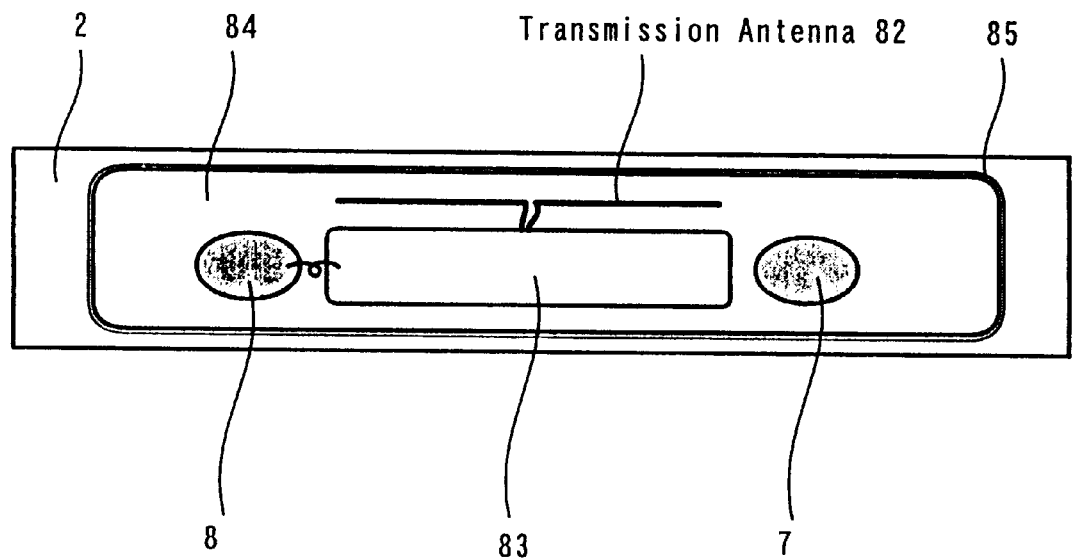
FIG. 11 is an explanatory view of the structure of the water drop detection sensor according to an eighth embodiment of the present invention, and in particular.

Next, as shown in FIG. 11, the water drop detection sensor 81 according to an eighth embodiment of the present invention comprises the light emitting means 5 for emitting the detection light, the light receiving means 6 for receiving that detection light, a transmission antenna 82 for transmitting the water drop detection signal and other signals through radios wave between equipment installed in the car, and a signal processing portion 83 for processing the water drop detection signals and so on which are received by the transmission antenna 82.

Moreover, the light emitting means 5 and the light receiving means 6 are covered with a radio wave-permeable case member 84 made of glass or resin in a box-like shape but opening the bottom surface thereof. The case member 84 is fixed on the interior side surface of the windshield 2 through the adhesive material 85 which also functions as the seal member, thereby defining a sealed space enclosed by the case member 84 and the windshield 2. Within the sealed space defined by the case member 84 and the windshield 2, there is enclosed or filled in a dehydration agent 86, such as a molecular sieve, or dry air, in place thereof.

The transmission antenna 82 and the signal processing portion 83 are provided on an inner surface of the case member 84 between light emitting means 5 and the light receiving means 6. The transmission antenna 82 and the signal processing portion 83 are connected, and the signal processing portion 83 is connected to the transmission antenna 82 as well. For example, when the case member 84 is made of glass having a refraction index of 1.48, the transmission antenna 82 manufactured on the glass is 17.5 mm in length, forming a so-called "half-wave" dipole antenna suitable for a radio wave 5.8 GHz in frequency. Also, the half-wave dipole antenna can be about 7.8 mm in length when the frequency of the radio wave is approximately 13 GHz.

The antenna can be made even smaller if material having a high dielectric constant, such as ceramic, is used for the substrate manufacturing the antenna thereon in place of glass. In a case where the frequency of the radio waves to be used is high, the antenna can be shortened, and it can be manufactured in the shape of a rod inside the case member 84.

Figure 12:
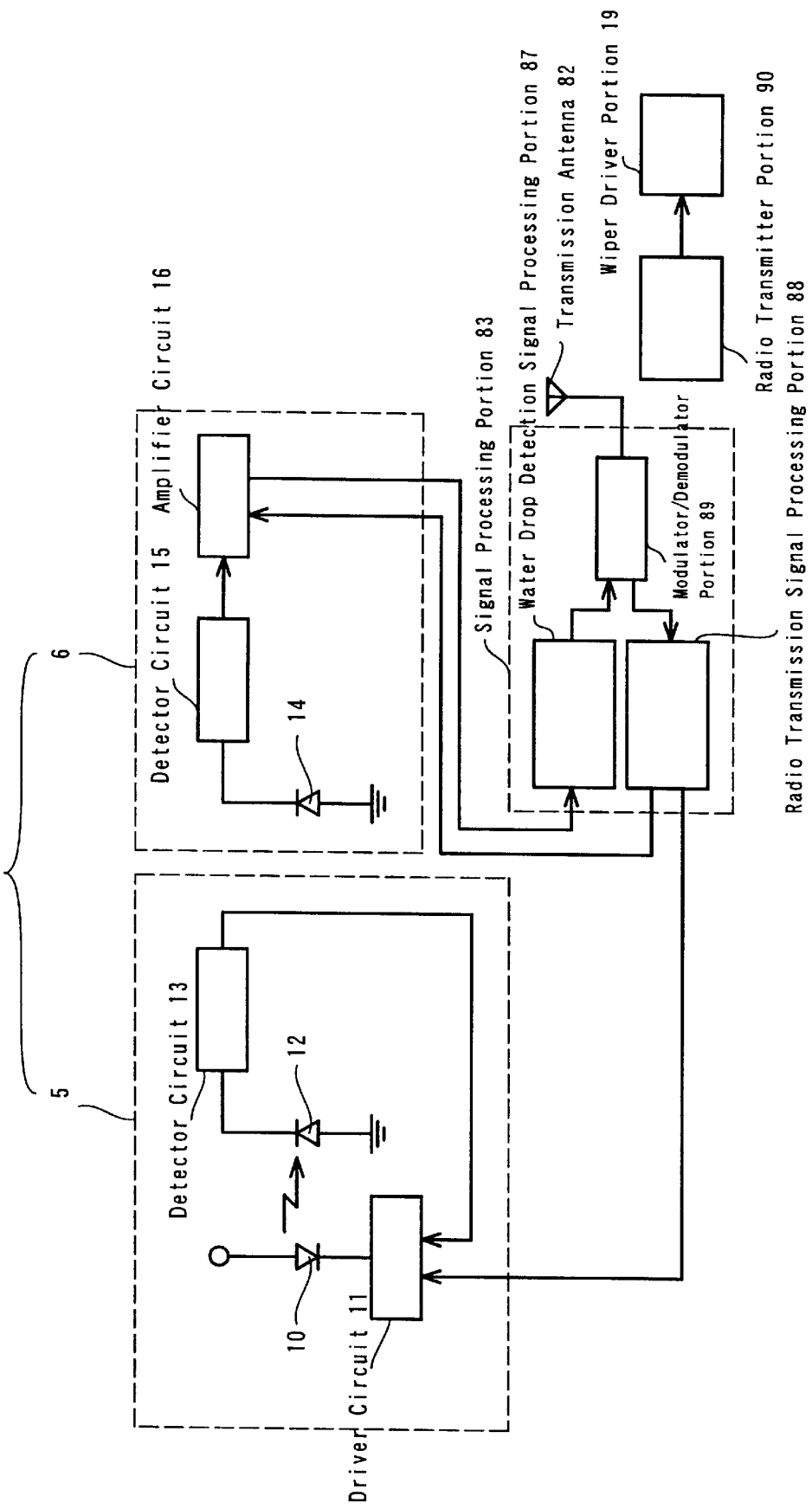
FIG. 12 is a structure view in which the water drop detection sensor according to the eighth embodiment of the present invention is applied to the wiper control system.

The signal processing portion 83 comprises, as shown in FIG. 12, a water drop detection signal processing portion 87 which can be constructed with a single purpose IC and/or memory, a radio transmission signal processing portion 88, which also can be constructed with a single purpose IC and/or memory, and cL modulator/demodulator portion 89. The water drop detection signal processing portion 87 is connected with the amplifier circuit 16 of the light receiving means 6, while the radio transmission signal processing portion 88 is connected with both the driver circuit 11 of the light emitting means 5 and the amplifier circuit 16 of the light receiving means 6.

Through the transmission antenna 82, transmission is carried out in relation to a light emission level signal of the light emitting means 5 and a sensitivity level signal of the light receiving means 6 between a radio wave transmitter portion 90 which is installed inside the car. The radio wave transmitter portion 90 is connected with the wiper driver portion 19, and therefore the wiper driver portion 19 controls the wiper 3 depending on the water drop detection signal.

However, the construction of the light emitting means 5 and the light receiving means 6, etc., is the same as that of the water drop detection sensor 1 shown in FIG. 2.

Explanation will be given of the operation of the water drop detection sensor 81 constructed as described above.

As shown in FIG. 12, the light receiving means 6 provides an output signal corresponding to the amount of water drops W as an input to the water drop detection signal processing portion 87 of the signal processing portion 83. Then, the output signal of the water drop detection signal processing portion 87 is transferred from the transmission antenna 82 through the modulator/demodulator portion 89 to the radio wave transmitter portion 90, so as to be inputted into the wiper driver portion 19. The wiper driver portion 19 turns the wiper 3 ON with a time interval depending on the amount of water drops W present (intermittent wiper operation), if the detected amount of water drops W is equal to or greater than the preset value thereof, while it switches the wiper OFF if the detected amount of water drops W is less than the preset value.

Meanwhile, when the light emission level signal of the light emitting means 5 and the sensitivity signal of the light receiving means 6 are transferred from the radio wave transmitter portion 90 for the purpose of setting up the light emitting means 5 and the light receiving means 6 into optimal conditions, then they are inputted into the radio transmission signal processing portion 88. Thus, the driver circuit 11 of the light emitting means 5 and the amplifier circuit 16 of the light receiving means 6 can be adjusted into desired conditions.

However, the functions or operations of the light emitting means 5 and the light receiving means 6, etc., are the same as those of the water drop detection sensor 1 shown in FIG. 2.

Figure 13A:
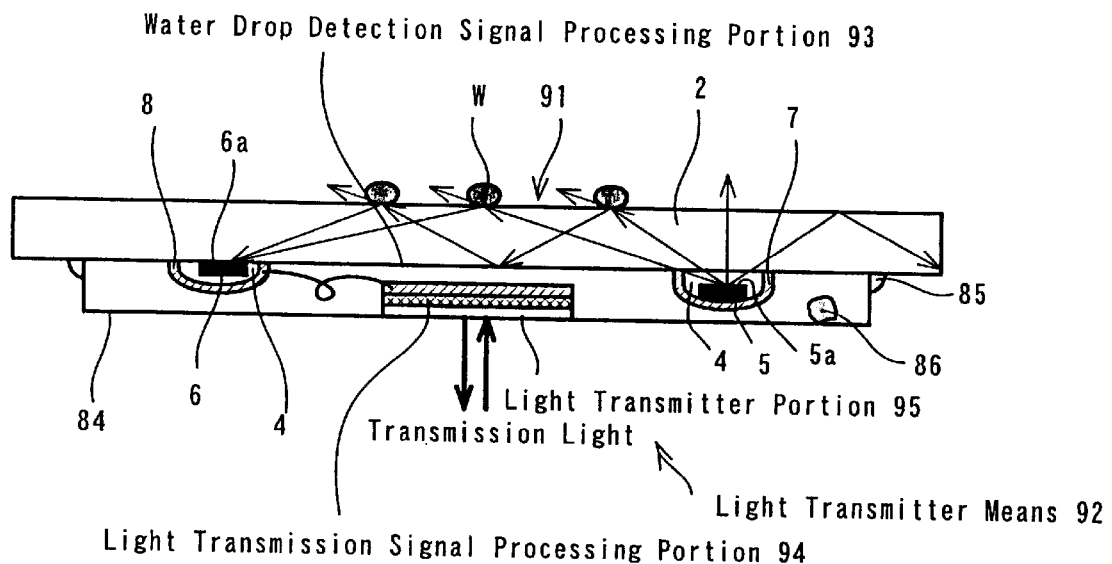
FIG. 13(a) is a cross-section view and FIG. 13(b) a rear view thereof.
Figure 13B:
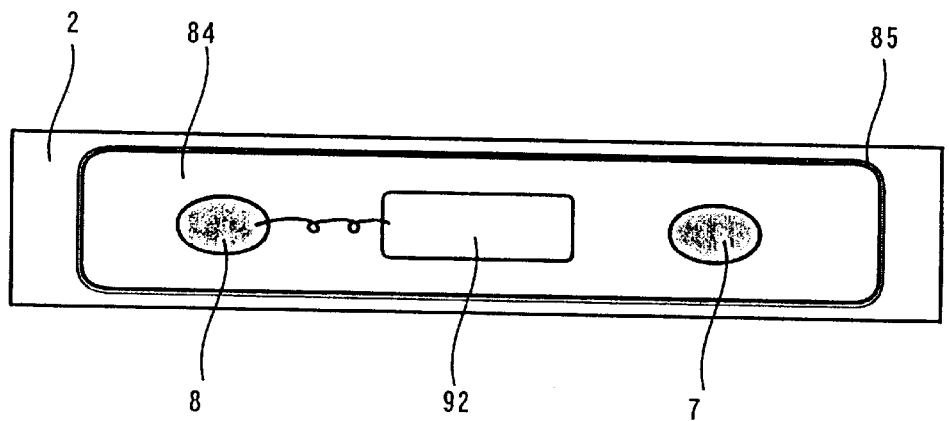
FIG. 13 is an explanatory view of the structure of the water drop detection sensor according to a ninth embodiment of the present invention, and in particular.

Also, as shown in FIG. 13, a water drop detection sensor 91 according to a ninth embodiment of the present invention detects the water drops W adhering to the windshield 2 depending upon the change in the amount of reflection light of the detection light, and in addition transmits the water drop detection signal and the other signals between the equipment inside the car via light (electromagnetic waves). However, the construction for detecting the water drops W is the same as that of the water drop detection sensor 81 shown in FIG. 11.

The case member 84 is made of light-permeable material, such as glass or resin. A light transmitting means 92 is mounted on an inside surface of the case member 84 between the light emitting means 5 and the light receiving means 6.

The light transmitting means 92 comprises a water detection signal processing portion 93, a light transmission signal processing portion 94, and a light transmitter portion 95, and they are arranged in layers.

Figure 14:
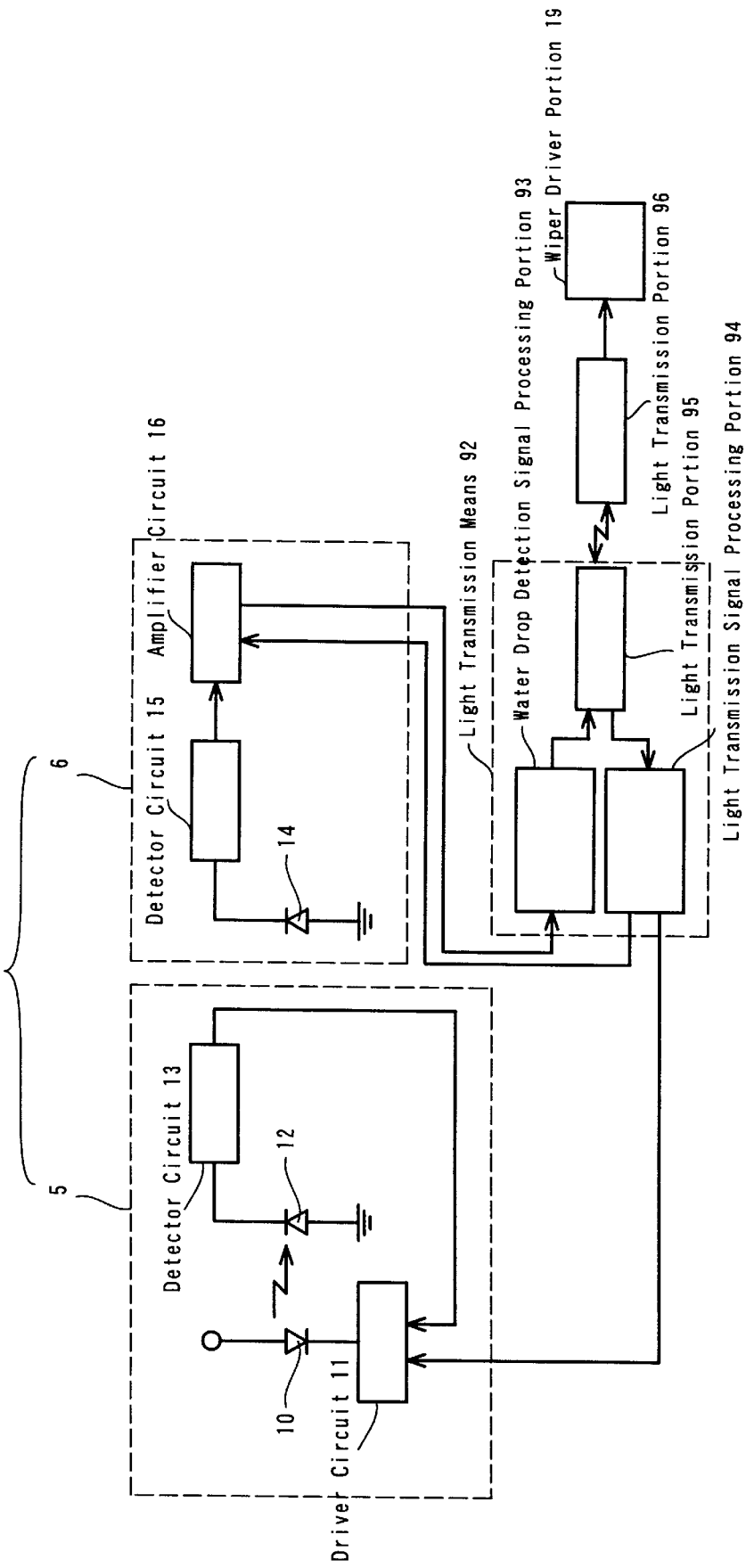
FIG. 14 is a structure view in which the water drop detection sensor according to the ninth embodiment of the present invention is applied to the wiper control system.

The light transmitting means 92 comprises, as shown in FIG. 14, the water drop detection signal processing portion 93 which can be constructed with a single purpose IC and/or memory, and the light transmission signal processing portion 94, which also can be constructed with a single purpose IC and/or memory, being connected to the light transmitter portion 95, respectively, wherein the water drop detection signal processing portion 93 is connected with the amplifier circuit 16 of the light receiving means 6, while the light transmission signal processing portion 94 is connected with both the driver circuit 11 of the light emitting means 5 and the amplifier circuit 16 of the light receiving means 6.

The light transmitter portion 95 carries out transmission in relation with the light emission level signal of the light emitting means 5 and the sensitivity level signal of the light receiving means 6 between a light transmitter portion 96 which is installed inside the car. The light transmitter portion 96 is connected with the wiper driver portion 19, and therefore the wiper driver portion 19 controls the wiper 3 depending on the water drop detection signal.

However, the operation of the water drop detection sensor 91 as constructed above is the same as that of the water drop detection sensor 81 shown in FIG. 11, except for transmitting the water drop detection signal and the others through the light between the equipment installed in the car.

Figure 15A:
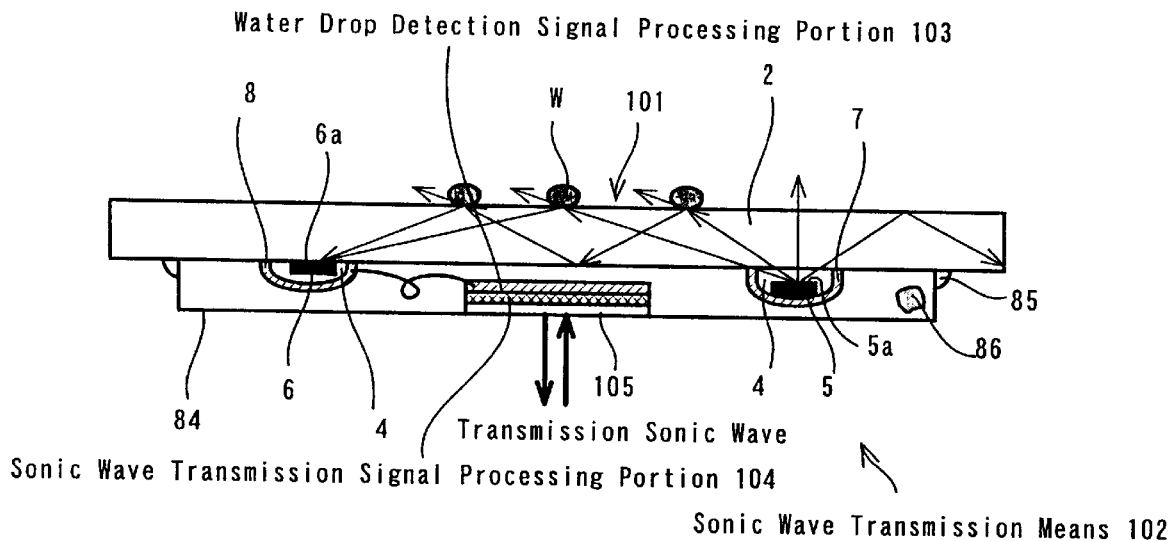
FIG. 15(a) is a cross-section view and FIG. 15(b) a rear view thereof.
Figure 15B:
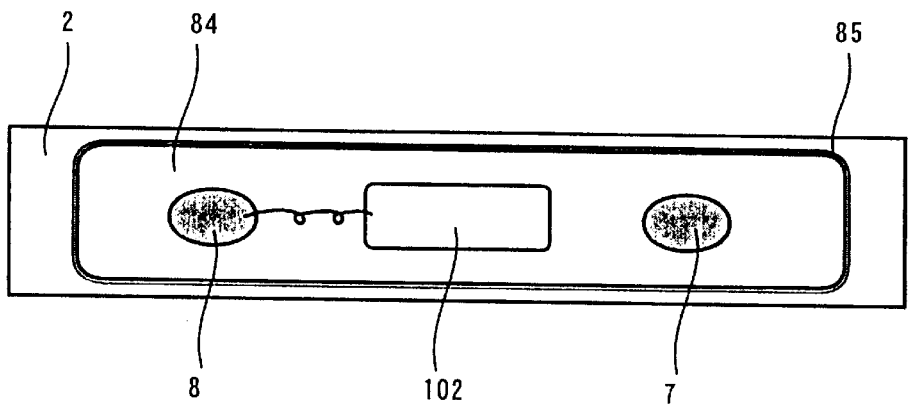
FIG. 15 is an explanatory view of the structure of the water drop detection sensor according to a tenth embodiment of the present invention, and in particular.

Further, as shown in FIG. 15, a water drop detection sensor 101 according to a tenth embodiment of the present invention detects the water drops W adhering to the windshield 2 depending upon the change in the amount of reflection light of the detection light, and in addition transmits the water drop detection signal and the other signals between the equipment inside the car via sonic waves. However, the construction for detecting the water drops W is the same as that of the water drop detection sensor 81 shown in FIG. 11.

The case member 84 is made of sonic wave-permeable material, such as glass or resin. A sonic wave transmitting means 102 is mounted on an inside surface of the case member between the light emitting means 5 and the light receiving means 6.

The sonic wave transmitting means 102 comprises a water detection signal processing portion 103, a sonic wave transmission signal processing portion 104 and a sonic wave transmitter portion 105, and they are arranged in layers.

Figure 16:
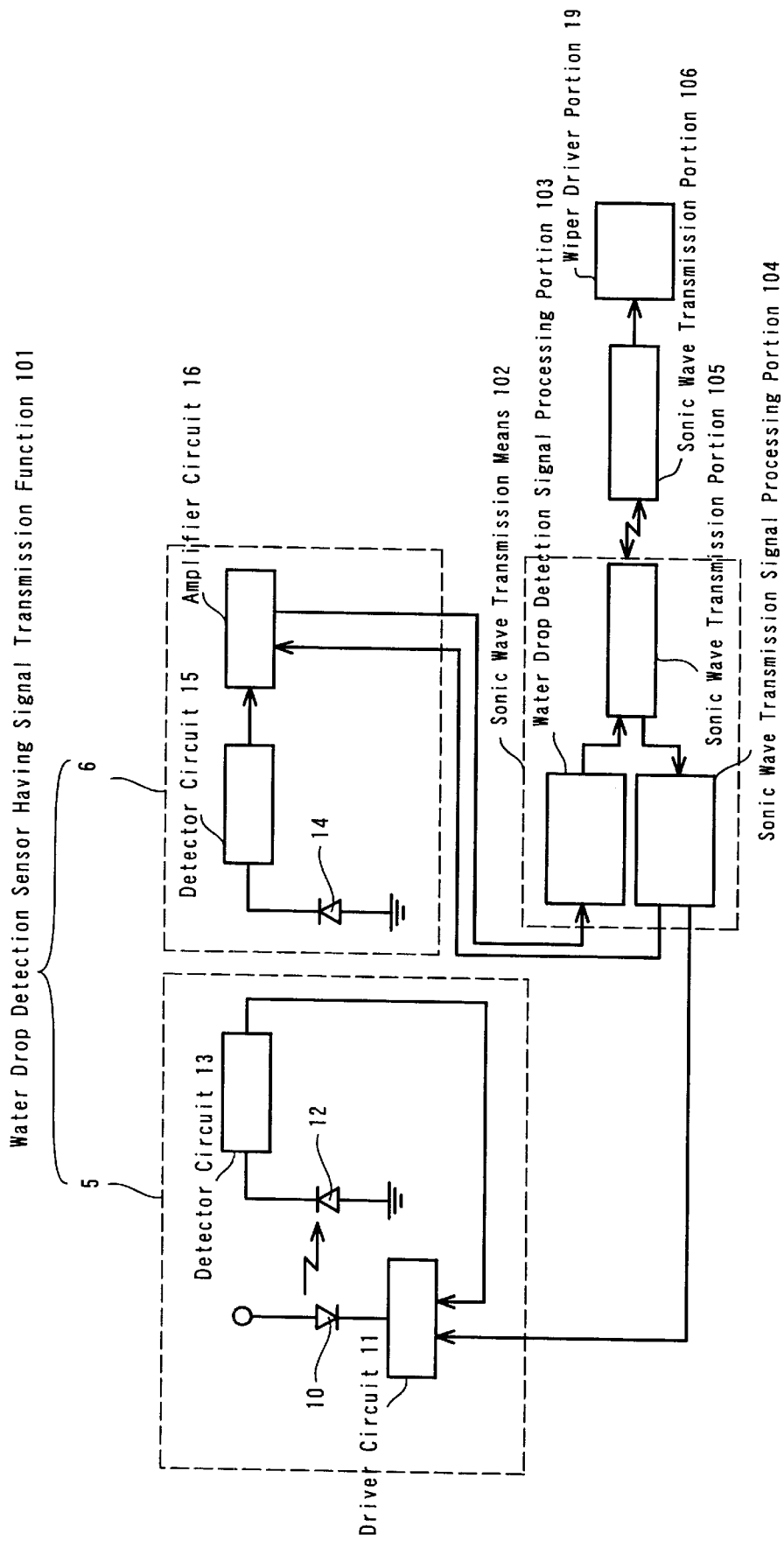
FIG. 16 is a structure view in which the water drop detection sensor according to the tenth embodiment of the present invention is applied to the wiper control system.

The sonic wave transmitting means 102 comprises, as shown in FIG. 16, the water drop detection signal processing portion 103 which can be constructed with a single purpose IC and/or memory, and the sonic wave transmission signal processing portion 104, which also can be constructed with a single purpose IC and/or memory, being connected to the light transmitter portion 95, respectively, wherein the water drop detection signal processing portion 93 is connected with the amplifier circuit 16 of the light receiving means 6, while the sonic wave transmission signal processing portion 104 is connected with both the driver circuit 11 of the light emitting means 5 and the amplifier circuit 16 of the light receiving means 6.

The sonic wave transmitter portion 105 carries out transmission in relation with the water drop detection signal, the light emission level signal of the light emitting means 5, and the sensitivity level signal of the light receiving means 6 between a sonic transmitter portion 106 which is installed inside the car. The sonic wave transmitter portion 106 is connected with the wiper driver portion 19, therefore the wiper driver portion 19 controls the wiper 3 depending on the water drop detection signal.

However, the operation of the water drop detection sensor 101 as constructed above is the same as that of the water drop detection sensor 81 shown in FIG. 11, except for transmitting the water drop detection signal and the others using the sonic waves between the equipment installed in the car.

Figure 17A:
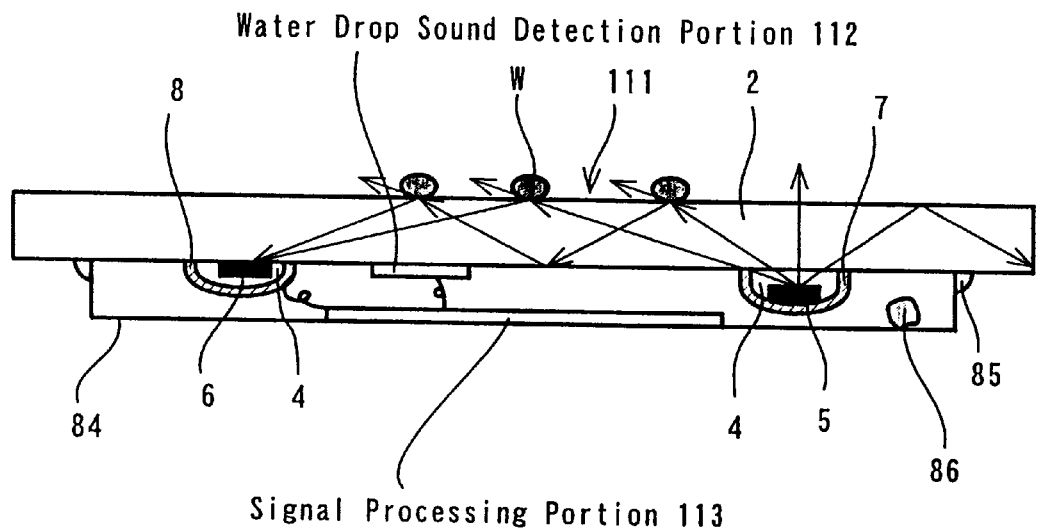
FIG. 17(a) is a cross-section view and FIG. 17(b) a rear view thereof.
Figure 17B:
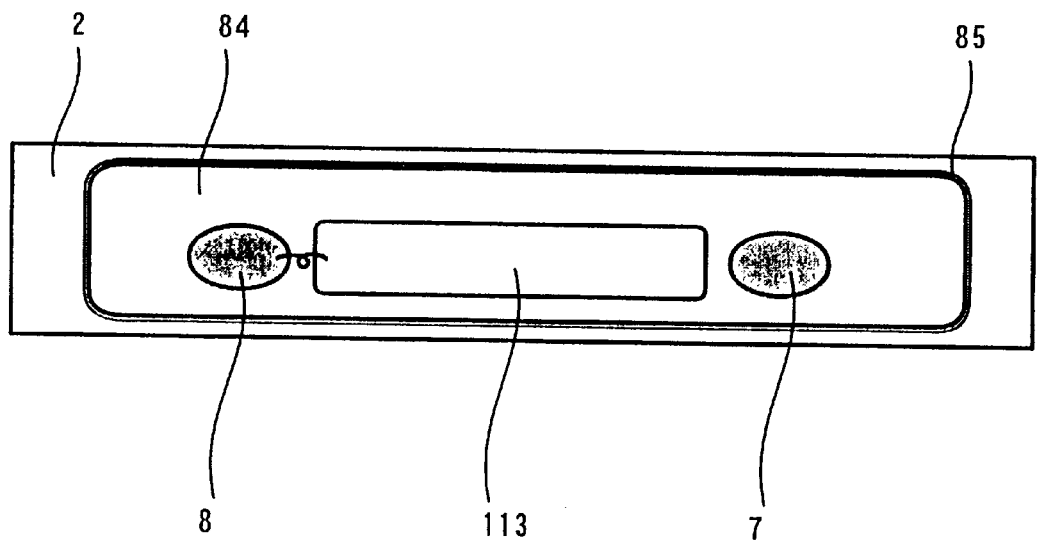
FIG. 17 is an explanatory view of the structure of the water drop detection sensor according to an eleventh embodiment of the present invention, and in particular.

Next, as shown in FIG. 17, the water drop detection sensor 111 according to an eleventh embodiment of the present invention comprises the light emitting means 5 and the light receiving means 6 mounted on the interior side surface of the windshield 2 with a predetermined distance thereinbetween, wherein the light emitting means 5 is buried in the adhesive material 4 so as to fix it and is opposite the light emitting surface thereof to the windshield 2, while the light receiving means 6 is fixed with the adhesive material 4 opposite the light receiving surface thereof to the windshield 2 in a similar manner.

The water drop detection sensor 111 further comprises a water drop sound detector 112 for detecting the sound occurring when the water drops W fall onto or land on (adhere on) the outer surface of the windshield 2, provided on the interior side surface thereof between the light emitting means 5 and the light receiving means 6.

Also, the light emitting means 5 and the light receiving means 6 and the water drop sound detector 112 are covered with a case member 84 made of glass or resin in a box-like shape which has an opening in the bottom surface thereof. The case member 84 is fixed on the interior side surface of the windshield 2 through the adhesive material 85 which also functions as the seal member, thereby defining a sealed space enclosed by the case member 84 and the windshield 2. Within the sealed space defined by the case member 84 and the windshield 2 is enclosed the dehydration agent 86, such as the molecular sieve, or dry air.

On the inside surface of the case member 84 is mounted a water drop detection signal processing portion 113, and, electrically connected to the water drop detection signal processing portion 113 are, the light receiving means 6 and the water drop sound detector 112. The water drop detection signal processing portion 113 calculates the amount of water drops present on the windshield from the water drop detection signal by means of the light emitting means 5 and the light receiving means 6, and also the water drop detection signal detected by the water drop sound detector 112, so as to provide an output signal.

Figure 18:
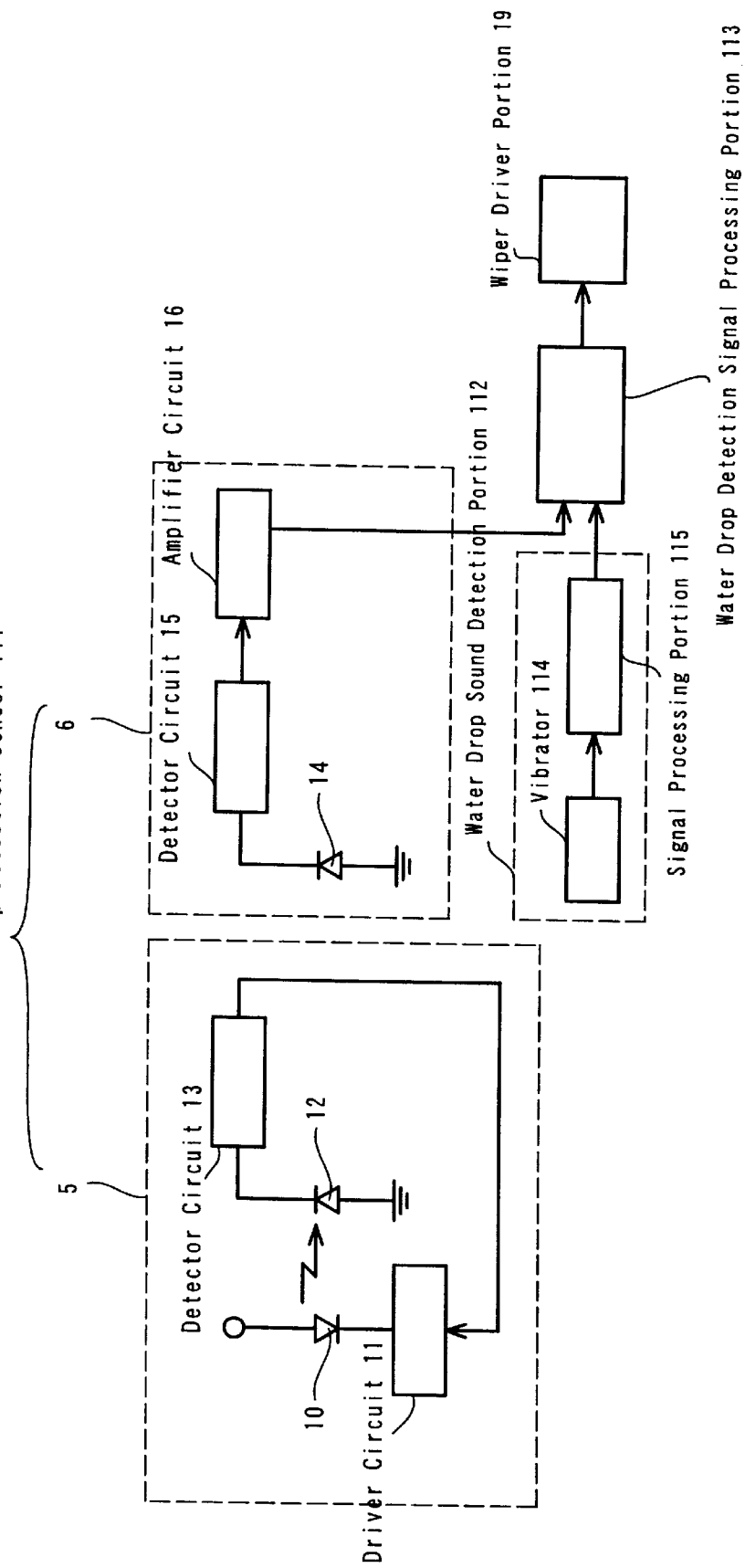
FIG. 18 is a structure view in which the water drop detection sensor according to the eleventh embodiment of the present invention is applied to the wiper control system.
Figure 19:
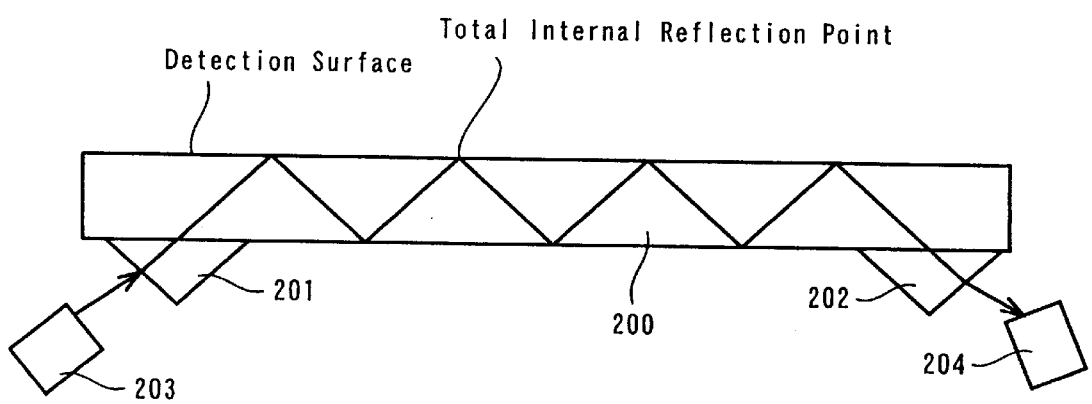
FIG. 19 is an explanatory view of the structure of the conventional water drop detection sensor.

The water drop sound detector 112 comprises, as shown in FIG. 18, a vibrator 114 for converting the sound of water drops falling onto the windshield into an electric signal, and a signal processing portion 115 which can be constructed with a single purpose IC and/or memory.

Both the amplifier circuit 16 and the signal processing portion 115 are connected with the water drop detection signal processing portion 113, which is connected to the wiper driver portion 19.

Explanation will be given of the operation of the water drop detection sensor 111 constructed as described above. However, since the functions of the light emitting means 5 and the light receiving means 6 are the same as those in the water drop detection sensor 1 shown in FIG. 2, explanation thereof will be omitted here.

When the water drops W adhere onto the outside surface of the windshield 2 opposite the water drop sound detector 112, a sound is generated due to collision thereupon, and this sound is detected by the vibrator 114, and is processed in the signal processing portion 115, thereby detecting the amount of water drops W present upon or adhering to the windshield.

As shown in FIG. 18, the light receiving means 6 provides the water drop detection signal processing portion 113 with the output corresponding to the amount of water drops W as an input thereto. Meanwhile, the water drop sound detector 112 also provides the water drop detection signal processing portion 113 with an output corresponding to the amount of water drops W as an input thereto.

However, when trying to detect the amount of water drops W by utilizing the reflection characteristics of light on the outside surface of the windshield, not only the adhesion of water drops but also the presence of dust and/or dirt is detected therewith.

On the other hand, when trying to detect the amount of water drops W by utilizing the sound of adhesion generated when they collide with or land upon the outside surface of the windshield 2, no dust and/or dirt present on the outside surface thereof is detected therewith.

Accordingly, comparing the water drop detection signal of the light receiving means 6 and the water drop detection signal of the water drop sound detector 112 within the water drop detection signal processing portion 113, it can be distinguished or discriminated whether water drops W or dirt—such as dust and/or miscellaneous foreign matter, are adhering onto the outside surface of the windshield 2.

Then, the water drop detection signal processing portion 113 provides the wiper driver portion 19 with the water drop detection signal of the light receiving means 6 only when both the light receiving means 6 and the water drop sound detector 112 provide output signals at a predetermined level. Otherwise, it is decided that no water drops W adhere onto the outside surface of the windshield 2, and the water drop detection signal processing portion 113 does not input the water drop detection signal of the light receiving means 6 to the wiper driver portion 19.

From the water drop detection signal inputted, the wiper driver portion 19 turns the wiper 3 ON with a time interval depending on the amount of water drops W present (intermittent wiping) if the detected amount of water drops W are equal to or greater than a preset value thereof, while it is switched OFF if the detected amount of water drops W are less than the preset value.

Further, as the light-permeable substrate comprising the water drop detection sensor according to the present invention, other than the windshield 2 for use in a car, there can be used a glass substrate, such as a rear window of a car or a door mirror thereof, a window glass of a railroad car, of a ship or of an aircraft, a window glass of building, a mirror of a washstand, or a traffic mirror standing at a corner or a curved road, etc. In other words, the invention can be applied to any glass substrate or resin substrate through which light is permeable.

Note that the water drop detection signal obtained from the water drop detection sensors can be applied also as a control signal for a wiper provided with the rear window or the door mirror, other than the wiper 3 provided with the windshield 2 of the car, and also can be used as a signal for initiating or regulating an anti-fog heater provided in the rear window or the door mirror of the car or in the mirror of a washstand.

What is claimed is:

1. A water drop detection sensor for detecting plural water drops adhering to or present upon a substrate and also for detecting ambient brightness, comprising:

a light-permeable substrate including an intermediate layer therein;

light emitting means for introducing detection light into said light-permeable substrate; and light receiving means for detecting reflected detection light, said reflected detection light being reflected by total internal reflection within said light-permeable substrate, and for detecting ambient light, wherein said light receiving means is provided on said light-permeable substrate, and a portion of said intermediate layer opposing to said light receiving means is formed with a reflection layer, in which layer is formed an opening for receiving the ambient light.

2. A water drop detection sensor for detecting plural water drops adhering to or present upon a substrate and also for detecting ambient brightness, comprising:

a light-permeable substrate;

light emitting means for introducing detection light into said light-permeable substrate;

light receiving means for detecting reflected detection light, said reflected detection light being reflected by total internal reflection within said light-permeable substrate; and ambient light receiving means for detecting ambient light, wherein said light receiving means and said ambient light receiving means are provided on said light-permeable substrate.

3. A water drop detection sensor for detecting plural water drops adhering to or present upon a substrate and also for detecting ambient brightness, comprising:

a light-permeable substrate including an intermediate layer therein;

light emitting means for introducing detection light into said light-permeable substrate;

light receiving means for detecting reflected detection light, said reflected detection light being reflected by total internal reflection within said light-permeable substrate; and ambient light receiving means for detecting ambient light, wherein said light receiving means and said ambient light receiving means are provided on said light-permeable substrate, and a portion of said intermediate layer opposing to said light receiving means is formed with a reflection layer, in which layer is formed an opening for receiving the ambient light.

4. A water drop detection sensor for detecting plural water drops adhering to or present upon a substrate and also for detecting ambient brightness, comprising:

a light-permeable substrate including an intermediate layer therein, on one surface of which the water drops adhere, and on the other surface of which is provided a non-pasted portion of black ceramic;

light emitting means for introducing detection light into said light-permeable substrate;

light receiving means for detecting reflected detection light, said reflected detection light being reflected by total internal reflection upon reflection point in the non-pasted portion of black ceramic within said light-permeable substrate; and ambient light receiving means for detecting ambient light, wherein said ambient light receiving means is provided in said non-pasted portion of black ceramic through an air layer.

5. A water drop detection sensor for detecting plural water drops adhering to or present upon a substrate and also for detecting ambient brightness, comprising:

a light-permeable substrate including an intermediate layer therein, on one surface of which the water drops adhere, and on the other surface of which is provided a non-pasted portion of black ceramic;

light emitting means for introducing detection light into said light-permeable substrate;

light receiving means for detecting reflected detection light, said reflected detection light being reflected by total internal reflection upon reflection point in the non-pasted portion of black ceramic within said light-permeable substrate; and ambient light receiving means for detecting ambient light, wherein said ambient light receiving means is provided in said non-pasted portion of black ceramic except the reflection point therein.

6. A water drop detection sensor for detecting plural water drops adhering to or present upon a substrate and also for detecting ambient brightness, comprising:

a light-permeable substrate including an intermediate layer therein, on one surface of which the water drops adhere;

light emitting means for introducing detection light into said light-permeable substrate;

light receiving means for detecting reflected detection light, said reflected detection light being reflected by total internal reflection within said light-permeable substrate; and ambient light receiving means for detecting ambient light, wherein said light emitting means, said light receiving means, and said ambient light receiving means are provided on the other side of said light-permeable substrate, and a portion of said intermediate layer is formed with a reflection layer, located between said light emitting means and said light receiving means.

7. A water drop detection sensor as defined in any one of claims 1 to 6, wherein said light-permeable substrate is a windshield, and said water drop detection sensor detects an amount of water drops adhering onto said windshield to provide a control signal to a wiper driver portion, as well as detects an amount of ambient light to provide a control signal to a headlight driver portion.

8. A water drop detection sensor as defined in any one of claims 1 to 6, wherein said light-permeable substrate is a windshield, and said water drop detection sensor detects an amount of water drop adhering onto said windshield and an amount of the ambient light to provide a control signal to a wiper driver portion.

9. A water drop detection sensor for detecting plural water drops adhering to or present upon a substrate and also for transferring a water drop detection signal and other signals between other equipment through radio waves, comprising:

a light-permeable substrate;

light emitting means for introducing detection light into said light-permeable substrate;

light receiving means for detecting reflected detection light, said reflected detection light being reflected by total internal reflection within said light-permeable substrate;

a transmission antenna for transmitting the signals between the other equipment through radio waves; and a signal processing portion for processing at least the water drop detection signal, wherein said light emitting means and said light receiving means are provided on said light-permeable substrate, and said transmission antenna and said signal processing portion are provided near said light emitting means and said light receiving means.

10. A water drop detection sensor for detecting plural water drops adhering to or present upon a substrate and also for transferring a water drop detection signal and other signals between other equipment through light waves, comprising:

a light-permeable substrate;

light emitting means for introducing detection light into said light-permeable substrate;

light receiving means for detecting reflected detection light, said reflected detection light being reflected by total internal reflection within said light-permeable substrate; and a light transmission means for transmitting the signals between the other equipment through radio waves, wherein said light emitting means and said light receiving means are provided on said light-permeable substrate, and said light transmission means is provided near said light emitting means and said light receiving means.

11. A water drop detection sensor for detecting plural water drops adhering to or present upon a substrate and also for transferring a water drop detection signal and other signals between other equipment through sonic waves, comprising:

a light-permeable substrate;

light emitting means for introducing detection light into said light-permeable substrate;

light receiving means for detecting reflected detection light, said reflected detection light being reflected by total internal reflection within said light-permeable substrate; and a sonic wave transmission means for transmitting the signals between the other equipment through sonic waves, wherein said light emitting means and said light receiving means are provided on said light-permeable substrate, and said sonic wave transmission means is provided near said light emitting means and said light receiving means.

12. A water drop detection sensor for detecting plural water drops adhering to or present upon a substrate and also for detecting sound when water drops fall onto or adhere onto said substrate, comprising:

a light-permeable substrate;

light emitting means for introducing detection light into said light-permeable substrate;

light receiving means for detecting reflected detection light, said reflected detection light being reflected by total internal reflection within said light-permeable substrate; and water drop sound detecting means for detecting the sound of water drops falling on or adhering to said light-permeable substrate, wherein said light emitting means, said light receiving means, and said water drop sound detecting means are provided on said light-permeable substrate.

* * * * *